（12） United States Patent
Alanine et al.

(10) Patent No.: US 6,359,138 B1
(45) Date of Patent: Mar. 19, 2002

(54) 4-HYDROXY-PIPERIDINE DERIVATIVES

(75) Inventors: Alexander Alanine, Riedisheim (FR); Bernd Büttelmann, Schopfheim (DE); Marie-Paule Heitz Neidhart, Hagenthal le Bas; Emmanuel Pinard, Linsdorf, both of (FR); René Wyler, Zürich (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 08/976,540

(22) Filed: Nov. 24, 1997

(30) Foreign Application Priority Data

Dec. 3, 1996 (EP) .............................. 96119345

(51) Int. Cl.[7] .......................................... C07D 401/06
(52) U.S. Cl. ...................... 546/201; 546/196; 546/200; 546/202; 546/205; 546/206; 546/210
(58) Field of Search ................................ 546/196, 200, 546/201, 202, 205, 206, 210

(56) References Cited

U.S. PATENT DOCUMENTS

| 3,476,760 A | | 11/1969 | Kaiser et al. |
| 3,506,671 A | * | 4/1970 | Kaiser, III et al. ........ 260/294.7 |
| 3,557,123 A | * | 1/1971 | Kaiser, IV et al. .......... 260/290 |
| 3,558,636 A | * | 1/1971 | Kaiser, II et al. ......... 260/293.4 |
| 4,016,281 A | | 4/1977 | Jonas et al. |
| 4,140,781 A | | 2/1979 | Huebner |
| 4,745,114 A | | 5/1988 | Elliott et al. |
| 5,326,771 A | | 7/1994 | Heine et al. |
| 5,436,255 A | | 7/1995 | Butler |

FOREIGN PATENT DOCUMENTS

| DE | 1 695 836 | 2/1968 |
| DE | 25 07 782 | 2/1975 |
| DE | 26 27 616 | 6/1976 |
| DE | 36 20 354 | 6/1986 |
| DE | 36 20 408 | 6/1986 |
| DE | 0 546 389 | 11/1992 |
| GB | 2 176 782 | 1/1987 |
| WO | WO 91 17156 | 11/1991 |

OTHER PUBLICATIONS

Bertocci, et al., *Proc. Natl. Acad. Sci. USA*, 88:1416–1420 (1991).
Bertrand, et al., *Methods in Neurosciences*, 4:174–193 (1991).
Green, T., *Protective Groups in Organic Synthesis*, Chapter 7, pp. 218–287 (1981).
Hollmann and Heinemann, *Annu. Rev. Neurosci.*, 17:31–109 (1994).
Sigel, et al., *J. Biol. Chem.*, 269:8204–8208 (1994).

* cited by examiner

Primary Examiner—Patricia L. Morris
(74) Attorney, Agent, or Firm—George W. Johnston; Patricia S. Rocha-Tramaloni; Arthur D. Dawson

(57) ABSTRACT

The present invention relates to 4-hydroxy-piperidine derivatives of the general formula

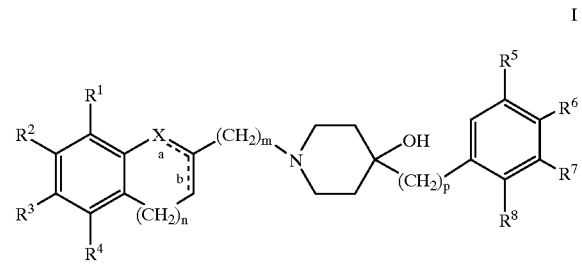

wherein X denotes —O—, —NH—, —CH$_2$—, —CH=, —CHOH—, —CO—, —S—, —SO— or —SO$_2$—;

$R^1$–$R^4$ are, independently from each other, hydrogen, hydroxy, lower-alkyl-sulfonylamino, 1- or 2-imidazolyl or acetamido;

$R^5$–$R^8$ are, independently from each other, hydrogen, hydroxy, lower-alkyl, halogen, lower-alkoxy, trifluoromethyl or trifluoromethyloxy;

a and b may be a double bond, provided that when "a" is a double bond, "b" cannot be a double bond;

n is 0–2;

m is 1–3;

p is 0 or 1 and to pharmaceutically acceptable addition salts thereof.

Compounds of the present invention are NMDA(N-methyl-D-aspartate)-receptor subtype selective blockers, which can be used in mediating processes underlying development of CNS including learning and memory formation and function.

2 Claims, No Drawings

4-HYDROXY-PIPERIDINE DERIVATIVES

BACKGROUND OF THE INVENTION

Under pathological conditions of acute and chronic forms of neurodegeneration overactivation of NMDA receptors is a key event for triggering neuronal cell death. NMDA receptors are composed of members of two subunit families, namely NR-1 (8 different splice variants) and NR-2 (A to D) originating from different genes. Members from the two subunit families show a distinct distribution in different brain areas. Heteromeric combinations of NR-1 members with different NR-2 subunits result in NMDA receptors displaying different pharmaceutical properties. Possible therapeutic indications for NMDA receptor subtype specific blockers include acute forms of neurodegeneration caused, e.g., by stroke and brain trauma, and chronic forms of neurodegeneration such as Alzheimer,s disease, Parkinson,s disease, Hantington,s disease, ALS (amyotrophic lateral sclerosis) and neurodegeneration associated with bacterial or viral infections.

The present invention relates to novel 4-hydroxy-piperidine derivatives, a process for their manufacture, and NMDA receptor subtype specific blocker compositions containing such 4-hydroxy-piperidine derivatives.

SUMMARY OF THE INVENTION

The present invention relates to 4-hydroxy-piperidine derivatives, exhibiting NMDA receptor subtype specific blocker activity.

The novel 4-hydroxy-piperidine derivatives of the present invention have the general formula (I),

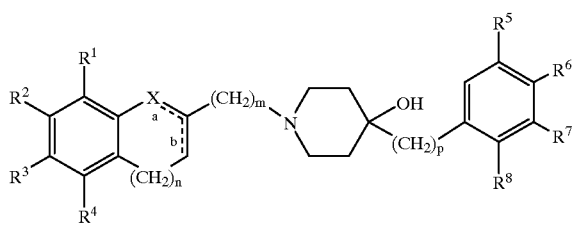

wherein
X denotes —O—, —NH—, —CH$_2$—, —CH═, —CHOH—, —CO—, —S—, —SO— or —SO$_2$—;
R$^1$–R$^4$ are, independently from each other, hydrogen, hydroxy, lower-alkyl-sulfonylamino, 1- or 2-imidazolyl or acetamido;
R$^5$–R$^8$ are, independently from each other, hydrogen, hydroxy, lower-alkyl, halogen, lower-alkoxy, trifluoromethyl or trifluoromethyloxy;
a and b may be a double bond, provided that when "a" is a double bond, "b" cannot be a double bond;
n is 0–2;
m is 1–3;
p is 0 or 1
and to pharmaceutically acceptable addition salts thereof.

The compounds of formula I and their salts are distinguished by valuable therapeutic properties. Compounds of the present invention are NMDA(N-methyl-D-aspartate)-receptor subtype selective blockers, which have a key function in modulating neuronal activity and plasticity which makes them key players in mediating processes underlying development of the CNS including learning and memory formation and function.

The objects of the invention are the compounds of formula I and pharmaceutically acceptable addition salts thereof, racemic mixtures and their corresponding enantiomers and the preparation of the above-mentioned compounds. Further objects of the present invention include medicaments containing the compounds and their manufacture as well as the treatment and control of illness using the compounds and medicaments set forth herein.

DETAILED DESCRIPTION OF THE INVENTION

The following definitions of the general terms are used the present specification and apply irrespective of whether the terms appear alone or in combination.

As used herein, the term "lower alkyl" denotes a straight or branched-chain alkyl group containing from 1 to 4 carbon atoms, for example, methyl, ethyl, propyl, isopropyl, n-butyl, i-butyl, 2-butyl and t-butyl.

The term "halogen" denotes chlorine, iodine, fluorine and bromine.

The term "lower alkoxy" denotes a group wherein the alkyl residue is as defined above.

The term "leaving group" has the meaning conventionally used, and refers to, for example, halogen, alkylsulfonyloxy, arylsulfonyloxy and the like. The most preferred leaving group in the present case is a halogen.

The term "pharmaceutically acceptable addition salts" embraces salts with inorganic and organic acids generally known to a person skilled in the art, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Compounds of formula I wherein X is —O—, —NH—, —CHOH or —CH$_2$— are preferred.

Exemplary preferred compounds in which X denotes —O—, are:
(RS)-1-(5-hydroxy-2,3-dihydro-benzofuran-2-ylmethyl)-4-(4-methyl-benzyl)-piperidine-4-ol,
(RS)-4-benzyl-1-(5-hydroxy-2,3-dihydro-benzofuran-2-ylmethyl)-piperidine-4-ol,
(RS)-4-(4-fluoro-benzyl)-1-(5-hydroxy-2,3-dihydro-benzofuran-2-ylmethyl)-piperidine-4-ol,
(RS)-4-(4-ethyl-benzyl)-1-(5-hydroxy-2,3-dihydro-benzofuran-2-ylmethyl)-piperidine-4-ol,
(S)-1-(5-hydroxy-2,3-dihydro-benzofuran-2-ylmethyl)-4-(4-methyl-benzyl)-piperidine-4-ol,
(S)-1-(5-hydroxy-2,3-dihydro-benzofuran-2-ylmethyl)-4-(4-chloro-benzyl)-piperidine-4-ol,
(RS)-N-[2-{4-hydroxy-4-(4-methyl-benzyl)-piperidine-1-ylmethyl}-2,3-dihydrobenzofuran-5-yl]-methane sulfonamide; and
(RS)-N-[2-{4-hydroxy-4-(4-methyl-benzyl)-piperidine-1-ylmethyl}-2,3-dihydrobenzofuran-5-yl]-methane sulfonamide.

Exemplary preferred compounds in which X denotes —CHOH— are:
(1RS,2RS) and (1RS,2SR)-2-[4-hydroxy-4-(4-methyl-benzyl)-piperidine-1-ylmethyl]-indan-1,5-diol,
(1RS,2RS)-1-(1,6-dihydroxy-1,2,3,4-tetrahydro-naphthalen-2-ylmethyl)-4-(4-methyl-benzyl)-piperidine-4-ol; and
(1RS,2RS)-2-(4-benzyl-4-hydroxy-piperidine-1-ylmethyl)-6-hydroxy-1,2,3,4-tetrahydronaphthalen-1-ol.

Exemplary preferred compounds in which X denotes —CH$_2$— are:

(RS)-1-(5-hydroxy-indan-2-ylmethyl)-4-(4-methyl-benzyl)-piperidine-4-ol; and (RS)-1-(6-hydroxy-1,2,3,4-tetrahydro-naphthalen-2-ylmethyl)-4-(4-methyl-benzyl)-piperidine-4-ol.

Another exemplary preferred compound in which X denotes —NH— is:

(RS)-2-[4-hydroxy-4-(4-methyl-benzyl)-piperidine-1-ylmethyl]-2,3-dihydro-1H-indol-5-ol.

The present compounds of formula I and their pharmaceutically acceptable salts can be prepared by methods known in the art, for example, by the processes (a-j) described below:

a) reacting a compound of the formula (II)

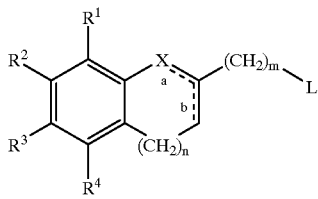

wherein $R^1$–$R^4$, X, a, b, n and m have the meaning given in general formula I and L is OH or a leaving group, for example, halogen or —O—tosyl, with a compound of the formula (III)

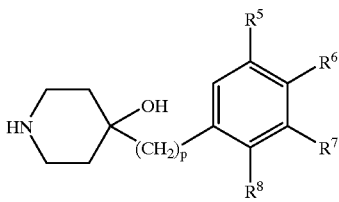

wherein $R^5$–$R^8$ and p have the meaning given in general formula I or b) reacting a compound of the formula (IV)

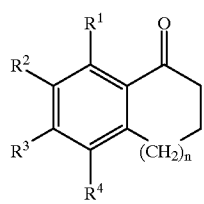

wherein the substituents have the meaning given in general formula I, with a compound of the formula (IIIA)

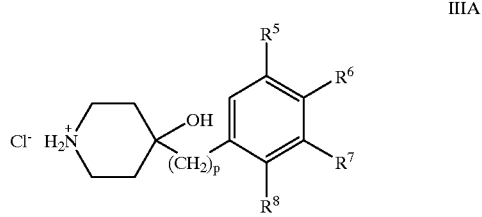

in the presence of paraformaldehyde to give a compound of the formula (IA)

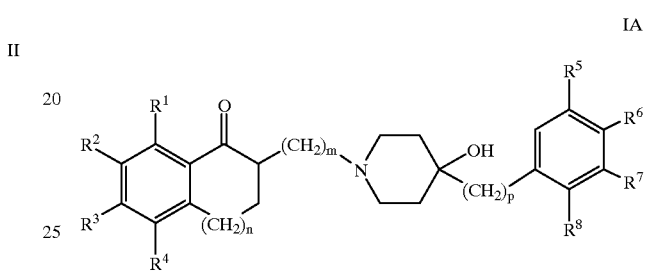

wherein m is 1 and the other substituents have the meaning given in general formula I, or c) dehydrating a compound of the formula (IB)

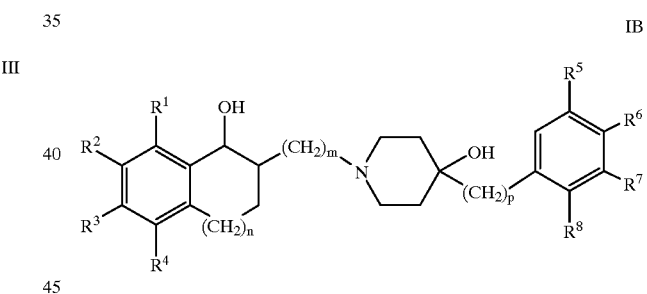

to give a compound of the formula (IC)

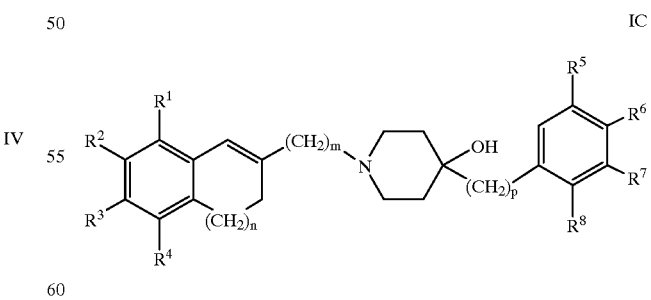

wherein m is 1 and the other substituents have the meaning given in general formula I, or d) reducing a compound of the formula IA to give a compound of the formula IB, or e) debenzylating a compound of the formula (V)

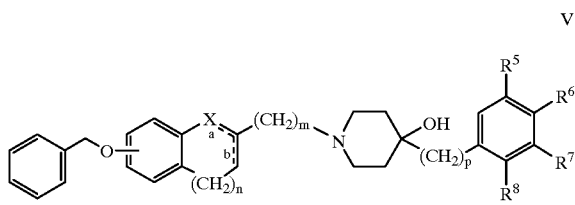

or f) reacting a compound of formula I, wherein one of $R^1-R^4$ is an amino group with a lower-alkyl-sulfonyl halogen to give a compound of formula I, wherein one of $R^1-R^4$ is a lower-alkyl-sulfonyl-amino group, or g) hydrogenating the isolated double bond in a compound of formula I, or h) cleaving off (a) hydroxy or amino protecting group(s) present as (a) substituent(s) $R^1-R^4$ or as X'=—N(protecting group)-, or i) oxidizing a compound of formula I, wherein X represents —S— or —SO— to yield the corresponding sulfonyl (—$SO_2$) compound; and j) if desired, converting the compound of formula I obtained into a pharmaceutically acceptable addition salt.

In accordance with process variant a), a mixture of a compound of formula II and of formula III, wherein the leaving group L in formula II is, for example, bromine, was dissolved in a suitable solvent, for example in DMF and heated to about 80–90° C. This reaction was carried out in the presence of a base, preferably triethylamine. The compound of formula I is then separated in conventional manner. When one of $R^1-R^4$ in formula II is a hydroxy group these groups are protected by groups conventionally used.

Examples of such groups are described in Green, T., *Protective Groups in Organic Synthesis*, Chapter 7, John Wiley and Sons, Inc. (1981), pp 218–287. Most preferred are the benzyloxy or alkyloxy groups. This reaction can be carried out by known methods, for example by hydrogenation with Pd/C (10%) or borontribromide-dichloromethane solution.

Process variant b) describes a process to obtain compounds of formula I wherein X is a —CO— group.

A compound of the formula IV is heated in a suitable solvent, for example in DMF together with a compound of formula IIIA in the presence of paraformaldehyde. This reaction is carried out at about 80° C. in conventional manner.

In accordance with process variant c), a compound of formula IB can be dehydrated in the presence of ethanolic HCl in conventional manner. Compounds of formula I in which "a" represents a double bond are obtained.

Variant d) describes a method for reducing of compounds of formula IA to give compounds of the formula IB. This reaction is carried out in conventional manner, preferably the reaction is carried out in the presence of $LiAlH_4$ in THF and at temperature of about 5–10° C.

In accordance with process variant e), a compound of formula I is obtained, wherein one of $R^1-R^4$ is hydroxy. This process is carried out by debenzylating a compound of formula V, provided that none of $R^5-R^8$ is halogen. The debenzylation is carried out in conventional manner. For example, a compound of formula V is dissolved in a suitable solvent or mixture of solvents such as ethanol and ethylacetate, and hydrogenated in the presence of Pd on C at room temperature and atmospheric pressure.

In accordance with process variant f), a compound of formula I can be obtained, wherein one of $R^1-R^4$ is a lower-alkyl-sulfonyl-amino group. This reaction is carried out by treating a compound of formula I, wherein one of $R^1-R^4$ is an amino group, with a lower-alkyl-sulfonylhalogen, such as methane sulfonylchloride, in a suitable solvent, such as methylene chloride, in the presence of pyridine at room temperature.

The hydrogenation of a compound of formula I, wherein one of "a" or "b" is a double bond in accordance with process variant g) is carried out in conventional manner, for example in the presence of Pd/C in ethylacetate under hydrogen atmosphere for about 24 hours at room temperature. Protecting groups, for example the hydroxy group, can be cleaved off by methods described above. Suitable protecting groups and methods for their cleavage will be familiar to any person skilled in the art; although of course there can be used only those protecting groups which can be cleaved off by methods under conditions of which other structural elements in the compounds are not affected.

The oxidation of compounds of formula I, wherein X is —S— or —SO—, is carried out in conventional manner. In accordance with process variant i), a compound of formula I, wherein X represents —S— or —SO—, is oxidized to yield the corresponding sulfonyl ($SO_2$—) compound. The oxidation can be carried out in the presence of Oxone® (potassium monopersulfate triple salt) at room temperature or in the presence of metachloroperbenzoic acid.

The addition salts of the compounds of formula I are especially well suited for pharmaceutical use.

As mentioned earlier, the compounds of formula I and their pharmaceutically usable addition salts possess valuable pharmacodynamic properties. They are NMDA-receptor subtype selective blockers, which have a key function in modulating neuronal activity and plasticity which makes them key players in mediating processes underlying development of CNS as well as learning and memory formation.

The compounds were investigated in accordance with the tests given hereinafter.

Method 1

3H-Ro 25-6981 Binding (Ro 25-6981 is [R-(R*, S*)]-a-(4-Hydroxy-phenyl)-b-methyl-4-(phenyl-methyl)-1-piperidine Propanol)

Male Füllinsdorf albino rats weighing between 150–200 g were used. Membranes were prepared by homogenization of the whole brain minus cerebellum and medulla oblongata with a Polytron (10.000 rpm, 30 seconds), in 25 volumes of a cold Tris-HCl 50 mM, EDTA 10 mM, pH 7.1 buffer. The homogenate was centrifuged at 48.000 g for 10 minutes at 4° C. The pellet was resuspended using the Polytron in the same volume of buffer and the homogenate was incubated at 37° C. for 10 minutes. After centrifugation the pellet was homogenized in the same buffer and frozen at −80° C. for at least 16 hours but not more than 10 days. For the binding assay the homogenate was thawed at 37° C., centrifuged and the pellet was washed three times as above in a Tris-HCl 5 mM, pH 7.4 cold buffer. The final pellet was resuspended in the same buffer and used at a final concentration of 200 μg of protein/ml. 3H-Ro 25-6981 binding experiments were performed using a Tris-HCl 50 mM, pH 7.4 buffer. For displacement experiments 5 nM of 3H-Ro 25-6981 were used and non specific binding was measured using 10 μM of tetrahydroisoquinoline and usually it accounts for 10% of the total. The incubation time was 2 hours at 4° C. and the assay was stopped by filtration on Whatmann GF/B glass fiber filters (Unifilter-96, Packard, Zütrich, Switzerland). The filters were washed 5 times with cold buffer. The radioactivity on the filter was counted on a Packard Topcount microplate scintillation counter after addition of 40 mL of microscint 40 (Canberra Packard S. A., Zürich, Switzerland).

The effects of compounds were measured using a minimum of 8 concentrations and repeated at least once. The pooled normalized values were analyzed using a non-linear regression calculation program which provide $IC_{50}$ with their relative upper and lower 95% confidence limits (RS1, BBN, USA).

Method 2

3H-Prazosine Binding

Male Füllinsdorf albino rats weighing between 150–200 g were used. Membranes were prepared by homogenization of the whole brain minus cerebellum and medulla oblongata with a Plytron (10.000 rpm, 30 seconds), in 25 volumes of a cold Tris-HCl 50 mM, EDTA 10 mM, pH 7.1 buffer. The homogenate was centrifuged at 48.000 g for 10 minutes at 4° C. The pellet was resuspended using the Polytron in the same volume of buffer and the homogenate was incubated at 37° C. for 10 minutes. After centrifugation the pellet was homogenized in the same buffer and frozen at −80° C. for at least 16 hours but not more than 10 days. For the binding assay the homogenate was thawed at 37° C., centrifuged and the pellet was washed three times as above in a Tris-HCl 5 mM, pH 7.4 cold buffer. The final pellet was resuspended in the same buffer and used at a final concentration of 200 µg of protein/ml.

3H-Prazosine binding experiments were performed using a Tris-HCl 50 mM, pH 7.4 buffer. For displacement experiments 0.2 nM of 3H-Prazosine were used and non specific binding was measured using 100 µM of Chlorpromazine. The incubation time was 30 minutes at room temperature and the assay was stopped by filtration on Whatman GF/B glass fiber filters (Unifilter-96, Canberra Packard S. A., Zürich, Switzerland). The filters were washed 5 times with cold buffer. The radioactivity on the filter was counted on a Packard Top-count microplate scintillation counter after addition of 40 ml of microscint 40 (Canberra Packard S. A., Zürich, Switzerland). The effects of compounds were measured using a minimum of 8 concentrations and repeated at least once. The pooled normalized values were analyzed using a non-linear regression calculation program which provide $IC_{50}$ with their relative upper and lower 95% confidence limits (RS1, BBN, USA).

Method 3

Electrophysiology on Recombinant NMDA Receptors cDNA clones coding for the subunits NR1C and NR2A of the NMDA receptor (see Hollmann and Heinemann, 1994, *Annu. Rev. Neurosci.* 17:31 for nomenclature of NMDA receptor subunits) were isolated from a rat brain λgt11 cDNA library as published elsewhere (Sigel et al., 1994, *J. Biol. Chem.* 269:8204). The clone for the subunit NR2B of the rat brain NMDA receptor was obtained from S. Nakanishi (Kyoto, Japan). The cDNAs encoding rat NR1C, NR2A and NR2B were subcloned into the expression vector pBC/CMV (Bertocci et al., 1991, *Proc. Natl. Acad. Sci. U.S.A.* 88:1416), placing transcription of the cDNA under control of the human cytomegalovirus promoter. CsCl-purified expression plasmids were mixed in a 1:3 ratio of NR1C:NR2A or NR1C:NR2B in injection buffer (88 mM NaCl, 1 mM KCl, 15 mM HEPES, at pH 7.0). Oocytes of South African frogs (*Xenopus laevis*) were used for expressing either a combination of the NR1C and NR2A subunits or the NR1C and NR2B subunits. 12 to 120 pg of a 1:3 (NR1C:NR2B) mixture of the respective cDNA species were injected into the nucleus of every oocyte. On the following two days the ion current through the NMDA receptor channels was measured in voltage clamp experiments for the methods of cDNA expression in oocytes and voltage-clamping (see, e.g., Bertrand et al., 1991, *Methods in Neurosciences* 4:174). The membrane potential was clamped to −80 mV and the receptors were activated by applying a modified Ringer,s solution containing the NMDA-receptor agonists L-glutamate (Glu) and glycine (Gly). Different agonist concentrations were chosen for either subunit combination to account for the different agonist sensitivities of the two types of receptors (2.7 µM Glu plus 0.9 µM Gly for NR 1C+NR2A and 1.3 µM Glu plus 0.07 µM Gly for NR1C+NR2B). The agonists were applied for 15 s intervals once every 2.5 min by rapid superfusion of the oocyte with agonist containing solution and the amplitude of the agonist-evoked current was measured immediately before the end of each application. After a series of initial control applications the antagonist to be tested was added to both, the basal Ringer,s and the agonist containing solution. The antagonist concentration applied to oocytes expressing the NR2A subunit was 10 µmol/l, whereas 0.1 µtmol/ were applied to the NR2B expressing oocytes. Four to six oocytes were tested for every compound and NMDA receptor subtype. Oocytes were exposed to the compounds for 5 to 30 min depending on the time needed for reaching an equilibrium block of the NMDA receptor current. For every oocyte the decrease of the current amplitude was expressed as a percentage of the control current measured before application of the compound. Figures in the table are arithmetic mean values of these percentage values.

The thus-determined activity of some compounds in accordance with the invention will be evident from the following table 1.

TABLE 1

| Compound (Example) # | 3H-Ro-25-6981 binding $IC_{50}$ (µM) | 3H-prazosine Binding $IC_{50}$ (µM) | Electrophysiology NR1C + NR2A % block by 10 µM | NR1C + NR2B % block by 0.1 µM |
|---|---|---|---|---|
| 1 | 0.040 | 3.0 | 65* | 72 |
| 2 | 0.020 | 3.2 | | |
| 4 | 0.050 | 2.5 | | |
| 5 | 0.040 | 4.0 | | |
| 7 | 0.012 | 6.0 | 12 | 89 |
| 13 | 0.014 | 6.0 | 8 | 93 |
| 14 | 0.005 | 6.0 | 9 | 90 |
| 16 | 0.023 | 5.0 | 6 | 86 |
| 19 | 0.055 | 3.2 | | |
| 21 | 0.055 | 6.6 | | |
| 22 | 0.040 | 6.5 | | |
| 23 | 0.040 | 2.3 | | |
| 27 | 0.026 | 6.0 | 15 | 91 |
| 29 | 0.023 | 11.0 | | |
| 30 | 0.020 | 0.8 | | |

*33% block at a concentration of 1 µM

(01) 1-(6-Hydroxy-3,4-dihydro-naphthalene-2-ylmethyl)-4-(4-methyl-benzyl)-piperidine-4-ol

(02) (RS)-1-(5-Hydroxy-2,3-dihydro-benzofuran-2-ylmethyl)-4-(4-methyl-benzyl)-piperidin-4-ol hydrochloride

(04) (RS)-4-Benzyl-1-(5-hydroxy-2,3-dihydro-benzofuran-2-ylmethyl)-piperidin-4-ol hydrochloide

(05) (RS)-4-(4-fluoro-benzyl)-1-(5-hydroxy-2,3-dihydro-benzofuran-2-ylmethyl)-piperidin-4-ol hydrochloride

(07) (RS)-4-(4-ethyl-benzyl)-1-(5-hydroxy-2,3-dihydro-benzofuran-2-ylmethyl)-piperidin-4-ol hydrochloride

(13) (S)-1-(5-Hydroxy-2,3-dihydro-benzofuran-2-ylmethyl)-4-(4-methyl-benzyl)-piperidin-4-ol hydrochloride

(14) (S)-1-(5-Hydroxy-2,3-dihydro-benzofuran-2-ylmethyl)-4-(4-chloro-benzyl)-piperidin-4-ol hydrochloride

(16) (1RS,2RS) and (IRS, 2SR)-2-[4-Hydroxy-4-(4-methyl-benzyl)-piperidine-1-ylmethyl]-indan-1,5-diol fumarate salt
(19) (RS)-1-(5-Hydroxy-indan-2-ylmethyl)-4-(4-methyl-benzyl)-piperidin-4-ol
(21) (RS)-2-[4-Hydroxy-4-(4-methyl-benzyl)-piperidin-1-ylmethyl]-2,3-dihydro-1H-indol-5-ol
(22) (RS)-N(2-[4-Hydroxy-4-{4-methyl-benzyl}-piperidin-1-ylmethyl]-2,3-dihydrobenzofuran-5-yl)-methane sulfonamide hydrochloride
(23) (RS)-N(2-[4-hydroxy-4-(4-methyl-benzyl)-piperidin-1-ylmethyl]-2,3-dihydrobenzofuran-5-yl)-methane sulfonamide hydrochloride
(27) (1RS, 2RS)-1-(1,6-Dihydroxy-1,2,3,4-tetrahydro-naphthalen-2-ylmethyl)-4-(4-methyl-benzyl)-piperidin-4-ol fumarate salt
(29) (1RS,2RS)-2-(4-benzyl-4-hydroxy-piperidin-1-ylmethyl)-6-hydroxy-1,2,3,4-tetrahydro-naphthalen-1-ol
(30) (RS)-1-(6-Hydroxy-1,2,3,4-tetrahydro-naphthalen-2-ylmethyl)-4-(4-methyl-benzyl)-piperidin-4-ol hydrochloride By screening, compounds of formula I could be identified as NMDA receptor subtype selective blockers and—for selected compounds—the preference for NMDAR-2B subunits could be demonstrated by eletrophysiological characterization using cloned NMDA receptor subtypes expressed oocytes.

The compounds of formula I and their salts, as herein described, can be incorporated into standard pharmaceutical dosage forms, for example, for oral or parenteral application with the usual pharmaceutical adjuvant materials, for example, organic or inorganic inert carrier materials, such as, water, gelatin, lactose, starch, magnesium stearate, talc, vegetable oils, gums, polyalkylene-glycols and the like. The pharmaceutical preparations can be employed in a solid form, for example, as tablets, suppositories, capsules, or in liquid form, for example, as solutions, suspensions or emulsions. Pharmaceutical adjuvant materials can be added and include preservatives stabilizers, wetting or emulsifying agents, salts to change the osmotic pressure or to act as buffers. The pharmaceutical preparations can also contain other therapeutically active substances.

The compounds of this invention may be administered in amounts that are pharmaceutically effective for the treatment of various acute forms of neurodegeneration. Particularly possible therapeutic indications for the NMDA receptor subtype specific blockers of this invention include chronic forms of neurodegeneration such as Alzheimer's disease, Parkinson's disease, Huntington's disease, and ALS (amyotrophic lateral sclerosis). Also treatable by the administration of pharmaceutically effective amounts of the NMDA receptor subtype specific blockers of this invention are acute forms of neurodegeneration caused by stroke and brain trauma, as well as neurodegeneration associated with bacterial or viral infections.

The daily dose of compounds of formula I to be administered varies with the particular compound employed, the chosen route of administration and the recipient. Representative of a method for administering the compounds of formula I is by the oral and parenteral type administration route. An oral formulation of a compound of formula I is preferably administered to an adult at a dose in the range of 150 mg to 1.5 g per day. A parenteral formulation of a compound of formula I is preferably administered to an adult at a dose in the range of 5 to 500 mg per day.

EXAMPLES

The following Examples illustrate the invention in more detail. All temperatures are given in degrees Celsius.

Preparation of Compounds and Starting Materials

In Examples 1–32 are described the processes for preparation of specific active compounds of formula I. The manufacture of these compounds is described in process variants a) to j) in their last process steps.

The schemes 1–5 show the preparation of different groups of compounds of formula II, which is a starting material for the last process step in the process variant a). The starting materials for the preparation of compounds of formula I are known or can be prepared by known methods, for example, according to the following Reaction Schemes. These reactions are described in more detail in Examples 33–75.

Scheme 1

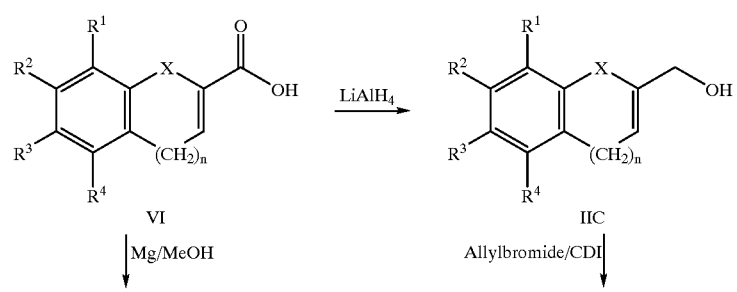

-continued
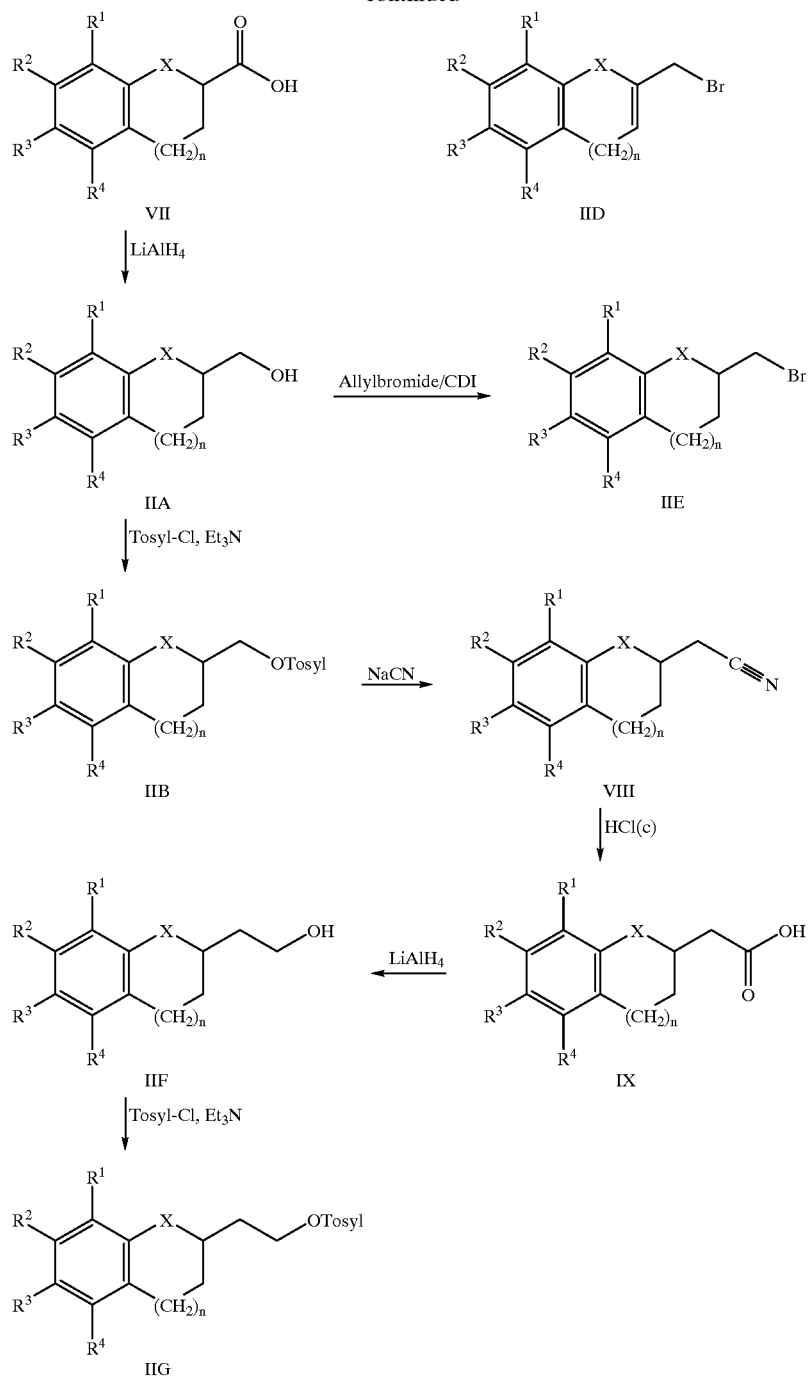
wherein the meaning of the substituents is as given in general formula I.

Scheme 2
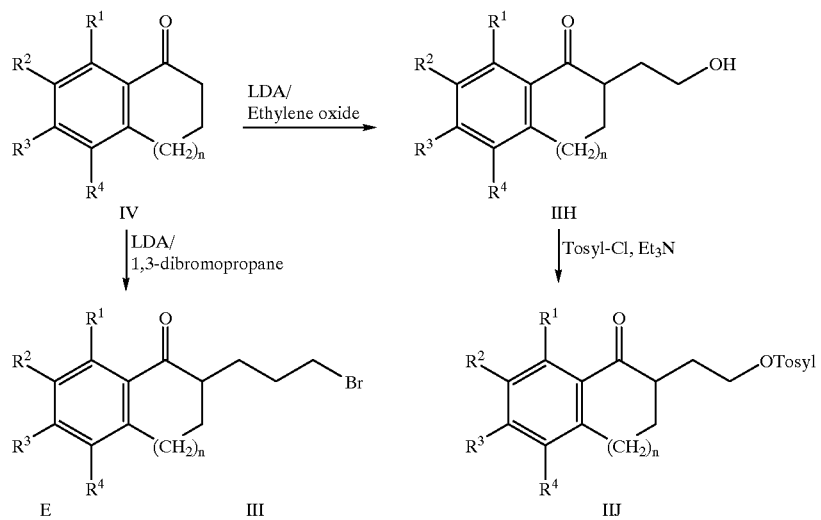
wherein the meaning of the substituents is as given in general formula I.
Scheme 3
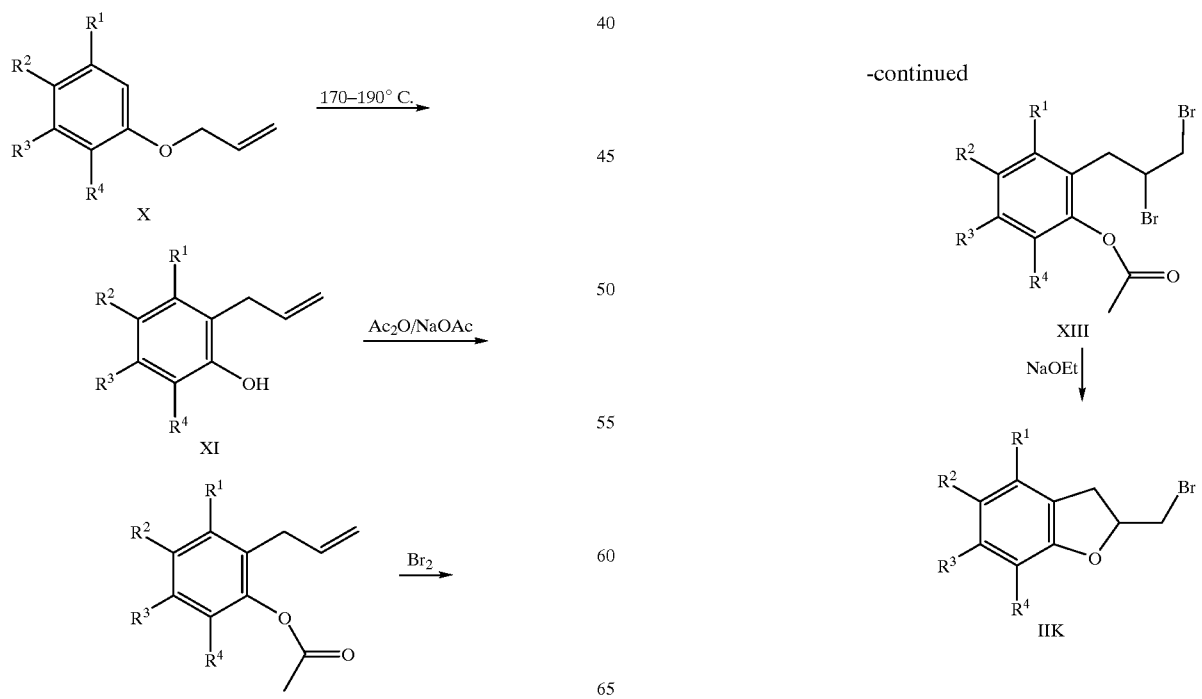
wherein the meaning of the substituents is as given in general formula I.

Scheme 4
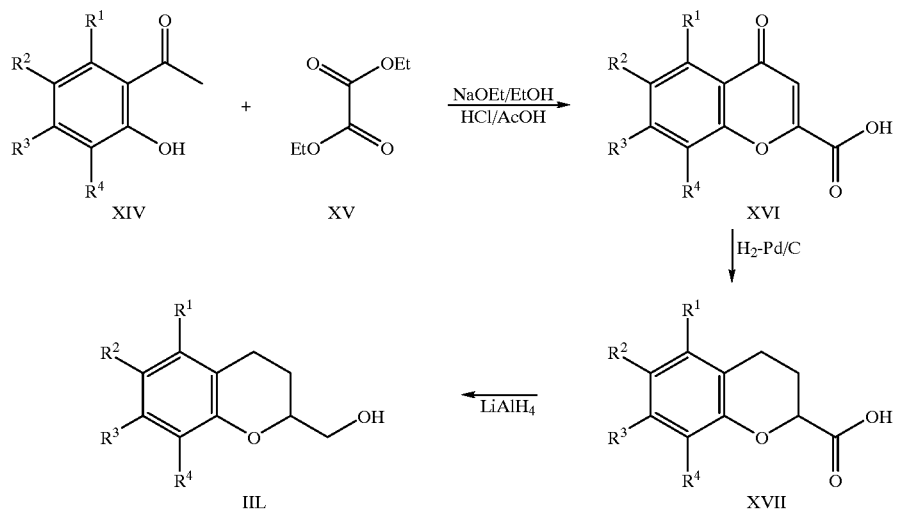
wherein the meaning of the substituents is as given in general formula I.
Scheme 5
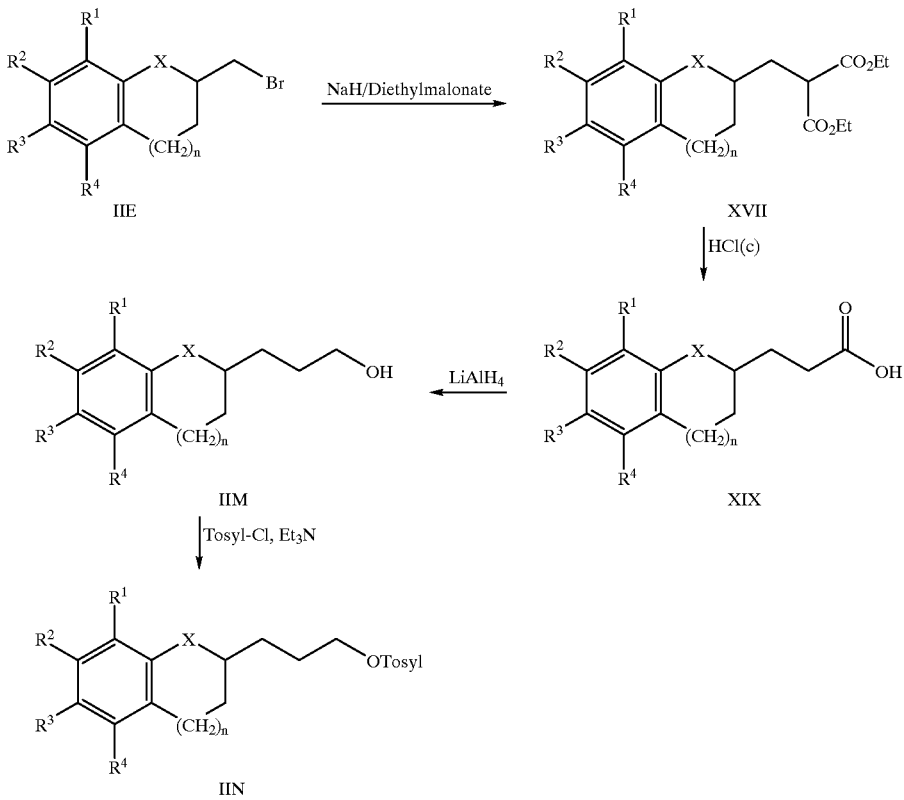
wherein the meaning of the substituents is as given in general formula I.
Example 1
1-(6-Hydroxy-3,4-dihydro-naphthalene-2-ylmethyl)-4-(4-methyl-benzyl)-pipgeridine-4-ol
(1RS, 2RS) (1-1,6-dihydroxy-1,2,3,4-tetrahydro-naphthalen-2-ylmethyl)-4-(4-methyl-benzyl)-piperidin-4-ol (286 mg, 0.75 mmol) was dissolved in EtOAc (25 ml) and treated with 6.4 N HCl in EtOH at RT. The mixture was then heated to reflux for 1 hr. After cooling, $H_2O$ was added (25 ml) and the mixture neutralised with 10% $NaHCO_3$ solution. The reaction mixture was then extracted with EtOAc (2×50 ml), washed with satd. NaCl solution (25 ml), dried with $Na_2SO_4$, filtered and evaporated to afford the title compound as a pink solid (238.8 mg, 0.657 mmol, 87%); MS: m/e=363.2 (M+H$^+$).

Example 2

(RS)-1-(5-Hydroxy-2,3-dihydro-benzofuran-2-ylmethyl)-4-(4-methyl-benzyl)-piperidin-4-ol hydrochloride (RS)-1-(5-benzyloxy-2,3-dihydro-benzofuran-2-ylmethyl)-4-(4-methyl-benzyl)-piperidin-4-ol (1.0 g, 2.2 mmol) in MeOH (100 ml) was hydrogenated with Pd/C (10%) (200 mg) for 17 hr at ambient temperature. Removal of the catalyst and evaporation afforded a yellow foam (720 mg, 2.0 mmol, 92%). This material (618 mg, 1.75 mmol) was then dissolved in EtOH (20 ml) and treated with 1.45N HCl/EtOH (1.1 eq.) at 0–5° C. to afford (RS)-1-(5-hydroxy-2,3-dihydro-benzofuran-2-ylmethyl)-4-(4-methyl-benzyl)-piperidin-4-ol hydrochloride as a whitelbeige foam, E/Z isomer mixture (679 mg, quant.), MS: m/e=354.2 (M+H$^+$). Following the Method of Example 2 the Compounds of Examples 3 to 12 were Prepared

Example 3

(RS)-1-(5-Hydroxy-2,3-dihydro-benzofuran-2-ylmethyl)-4-(4-methoxy-benzyl)-piperidin-4-ol hydrochloride The title compound MS: m/e=370.2 (M+H$^+$) was prepared from (RS)-1-(5-benzyloxy-2,3-dihydro-benzofuran-2-ylmethyl)-4-(4-methoxy-benzyl)-piperidin-4-ol.

Example 4

(RS)-4-Benzyl-1-(5-hydroxy-2,3-dihydro-benzofuran-2-ylmethyl)-piperidin-4-ol hydrochloride The title compound MS: m/e=340.2 (M+H$^+$) was prepared from (RS)-4-benzyl-1-(5-benzyloxy-2,3-dihydro-benzofuran-2-ylmethyl)-piperidin-4-ol.

Example 5

(RS)-4-(4-fluoro-benzyl)-1-(5-hydroxy-2,3-dihydro-benzofuran-2-ylmethyl)-piperidin-4-ol hydrochloride The title compound MS: m/e=358.2 (M+H$^+$) was prepared from (RS)-4-(4-fluoro-benzyl)-1-(5-hydroxy-2,3-dihydro-benzofuran-2-ylmethyl)-piperidin-4-ol.

Example 6

(RS)-4-(3,4-Dimethyl-benzyl)-1-(5-hydroxy-2,3-dihydro-benzofuran-2-ylmethyl)-piperidin-4-ol hydrochloride The title compound MS: m/e=368.2 (M+H$^+$) was prepared from (RS)-4-(3,4-dimethyl-benzyl)-1-(5-benzyloxy-2,3-dihydro-benzofuran-2-ylmethyl)-piperidin-4-ol.

Example 7

(RS)-4-(4-ethyl-benzyl)-1-(5-hydroxy-2,3-dihydro-benzofuran-2-ylmethyl)-piperidin-4-ol hydrochloride The title compound MS: m/e=368.2 (M+H$^+$) was prepared from (RS)-4-(4-ethyl-benzyl)-1-(5-benzyloxy-2,3-dihydro-benzofuran-2-ylmethyl)-piperidin-4-ol.

Example 8

(RS)-4-(4-Isopropyl-benzyl)-1-(5-hydroxy-2,3-dihydro-benzofuran-2-ylmethyl)-piperidin-4-ol hydrochloride The title compound MS: m/e=382.2 (M+H$^+$) was prepared from (RS)-4-(4-isopropyl-benzyl)-1-(5-benzyloxy-2,3-dihydro-benzofuran-2-ylmethyl)-piperidin-4-ol.

Example 9

(RS)-4-(2-Methyl-benzyl)-1-(5-hydroxy-2,3-dihydro-benzofuran-2-ylmethyl)-piperidin-4-ol hydrochloride The title compound MS: m/e=354.2 (M+H$^+$) was prepared from (RS)-4-(2-methyl-benzyl)-1-(5-benzyloxy-2,3-dihydro-benzofuran-2-ylmethyl)-piperidin-4-ol.

Example 10

(RS)-4-(2,4-Difluoro-benzyl)-1-(5-hydroxy-2,3-dihydro-benzofuran-2-ylmethyl)-piperidin-4-ol hydrochloride The title compound MS: m/e=376.2 (M+H$^+$) was prepared from (RS)-4-(2,4-difluoro-benzyl)-1-(5-benzloxy-2,3-dihydro-benzofuran-2-ylmethyl)-piperidin-4-ol.

Example 11

(RS)-4-(4-Trifluoromethoxy-benzyl)-1-(5-hydroxy-2,3-dihydro-benzofuran-2-ylmethyl)-piperidin-4-ol hydrochloride The title compound MS: m/e=424.2 (M+H$^+$) was prepared from (RS)-4-(4-trifluoro-methoxy-benzyl)-1-(5-benzyloxy-2,3-dihydro-benzofuran-2-ylmethyl)-piperidin-4-ol.

Example 12

(RS)-4-(3-Trifluoromethyl-benzyl)-1-(5-hydroxy-2,3-dihydro-benzofuran-2-ylmethyl)-piperidin-4-ol hydrochloride The title compound MS: m/e=408.2 (M+H$^+$) was prepared from (RS)-4-(3-trifluoro-methyl-benzyl)-1-(5-benzyloxy-2,3-dihydro-benzofuran-2-ylmethyl)-piperidin-4-ol.

Example 13

(S)-1-(5-Hydroxy-2,3-dihydro-benzofuran-2-ylmethyl)-4-(4-methyl-benzyl)-piperidin-4-ol hydrochloride (S)-1-(5-methoxy-2,3-dihydro-benzofuran-2-ylmethyl)-4-(4-methyl-benzyl)-piperidin-4-ol (2.10g, 5.71 mmol) dissolved in 50 ml of $CH_2Cl_2$ was cooled to −78° C. and 1M $BBr_3$—$CH_2Cl_2$ solution (12.5 ml, 2.2 eq.) was added dropwise under argon. The beige suspension was allowed to warm to ambient temperature over 30 min and then stirred for a further 1 hour, during which time a sticky yellow solid deposited. MeOH (10 ml) was then added to quench the reaction, followed by distilled $H_2O$ (100 ml) and satd. $NaHCO_3$ solution (25 ml); the mixture was then stirred vigorously for 15 min. The organic phase was separated, satd. NaCl solution (100 ml) was then added to the aqueous phase and extracted with $CH_2Cl_2$ (2×50 ml). The combined organic extracts were dried with $Na_2SO_4$ then filtered and evaporated. The resulting yellow foam was chromatographed over SiO$_2$ (Merck 230–400 mesh) eluting with CH$_2$Cl$_2$ followed by MeOH—CH$_2$Cl$_2$ (3:97) followed by MeOH—CH$_2$Cl$_2$ (7:93) (1.7 g, 4.81 mmol, 84% yield). (S)-1-(5-hydroxy-2,3-dihydro-benzofuran-2-ylmethyl)-4-(methyl-benzyl)-piperidin-4-ol (1.62 g, 4.58 mmol) was suspended in EtOH and treated with 1.1 eq of ethanolic HCl at 0–5° C. affording (S)-1-(5-hydroxy-2,3-dihydro-benzofuran-2-ylmethyl)-4-(4-methyl-benzyl)-piperidin-4-ol hydrochloride as a white foam and mixture of E/Z isomers (1.74 g, 4.46 mmol, 97%) MS: m/e=354.2 (M+H$^+$) [α]=+57.8° (c=1.0, EtOH)

Following the General Method of Example 13, Compound of Examples 14 and 15 were Prepared.

Example 14

(S)-1-(5-Hydroxy-2,3-dihydro-benzofuran-2-ylmethyl)-4-(4-chloro-benzyl)-piperidin-4-ol hydroehloride The title compound, MS: m/e=374.2 (M+H$^+$) [α]=+32.4° (c=1.0, DMF), >99% e.e. by chiral phase HPLC, was prepared from (S)-1-(5-methoxy-2,3-dihydro-benzofuran-2-ylmethyl)-4-(4-chloro-benzyl)-piperidin-4-ol.

Example 15

(R)-1-(5-Hydroxy-2,3-dihydro-benzofuran-2-ylmethyl)-4-(methyl-benzyl)-piperidin-4-ol Hydrochloride The title compound as a white foam and mixture of E/Z isomers (1.64 g, 4.20 mmol, 100%) MS: m/e=354.2 (M+H$^+$) [α]=−58.0° (c=1.0, EtOH) was prepared from (R)-1-(5-methoxy-2,3-dihydro-benzofuran-2-ylmethyl)-4-(methyl-benzyl)-piperidin-4-ol.

Example 16

(1RS,2RS) and (1RS, 2SR)-2-[4-Hydroxy-4-(4-methyl-benzyl)-piperidine-1-ylmethyl]-indan-1,5-diol Fumarate Salt (1RS,2RS) and (1RS, 2SR)-2-[4-benzyloxy-4-(4-methyl-benzyl)-piperidine-1-ylmethyl]-indan-1,5-diol (674 mg, 1.84 mmol) was taken up in EtOH (20 ml), fumaric acid (106 mg, 0.92 mmol) was added and the mixture stirred for 2 hr at RT, after evaporation of the solvent, (1RS,2RS) and (1RS, 2SR)-2-[4-hydroxy-4-(4-methyl-benzyl)-piperidine-1-ylmethyl]-indan-1,5-diol fumaric acid salt was obtained as a white foam (0.78 g, quant.), MS m/e=368.2 (M+H$^+$).

Example 17

(1RS,2RS) and (1RS, 2SR)-2-[4-hydroxy-4-(4-methyl-benzyl)-piperidine-1-ylmethyl -indan-1,5-diol A solution of (1RS,2RS)and (1RS,2SR)-2-[4-benzyloxy-4-(4-methyl-benzyl)-piperidine-1-ylmethyl]-indan-1,5-diol (0.83 g, 1.82 mmol) in MeOH (100 ml) and Pd/C 10% (100 mg) was stirred vigorously under a hydrogen atmosphere for 1 hr at ambient temperature. After removal of the catalyst and evaporation of the solvent the title compound (1RS, 2RS) and (1RS, 2SR)-2-[4-hydroxy-4-(4-methyl-benzyl)-piperidine-1-ylmethyl]-indan-1,5-diol (664 mg, 1.81 mmol, 99%) was afforded as a white amorphous foam, (1:1) mixture of diastereoisomers, MS m/e=368.2 (M+H$^+$).

Example 18

(RS)-1-(5-Hydroxy-indan-2-ylmethyl)-4-(4-methyl-benzyl)-piperidin-4-ol Hydrochloride (RS)-1-(5-hydroxy-indan-2-ylmethyl)-4-(4-methyl-benzyl)-piperidin-4-ol (177 mg, 0.503 mmol) was dissolved in EtOH and ethanolic HCl (1.7 eq) was added, the product was precipitated after 15 min. by addition of diethylether while cooling to 4° C. The product was afforded as a white solid-foam (RS)-1-(5-hydroxy-indan-2-ylmethyl)-4-(4-methyl-benzyl)-piperidin-4-ol hydrochloride (95.7 mg, 0.246 mmol, 49%) Mp. 88–90° C., MS m/e=352.2 (M+H$^+$).

Example 19

(RS)-1-(5-Hydroxy-indan-2-ylmethyl)-4-(4-methyl-benzyl)-piperidin-4-ol 1-(6-Hydroxy-1H-inden-2-ylmethyl)-4-(4-methyl-benzyl)-piperidin-4-ol (256 mg, 0.732 mmol) and Pd/C 10% (50 mg) in EtOAc (15 ml) was stirred vigorously under a hydrogen atmosphere for 24 hr at RT. Removal of the catalyst and evaporation of the solvent afforded (RS)-1-(5-hydroxy-indan-2-ylmethyl)-4-(4-methyl-benzyl)-piperidin-4-ol as a colourless oil (235 mg, 0.667 mmol, 91%), MS m/e=352.2 (M+H$^+$).

Example 20

1-(6-Hydroxy-1H-inden-2-ylmethyl)-4-(4-methyl-benzyl)-piperidin-4-ol (1RS,2RS) and (1RS, 2SR)-2-[4-hydroxy-4-(4-methyl-benzyl)-piperidine-1-ylmethyl]-indan-1,5-diol (310 mg, 0.84 mmol) and ethanolic HCl (5 eq.) was heated in EtOAc (30 ml) at 65° C. for 1.5 hr. Distilled H$_2$O (30 ml) and 10% NaHCO$_3$ (30 ml) was added and the mixture shaken, the aqueous phase was further extracted with EtOAc (2×20 ml) and the combined organic extracts were washed with satd. NaCl solution (30 ml), dried (Na2SO$_4$) and filtered. Evaporation of the solvent afforded 1-(6-hydroxy-1H-inden-2-ylmethyl)-4-(4-methyl-benzyl)-piperidin-4-ol as a beige solid (308 mg, 0.84 mmol, 100%) Mp. 154–157° C., MS m/e=350.2 (M+H$^+$).

Example 21

(RS)-2-[4-Hydroxy-4-(4-methyl-benzyl)-piperidin-1-ylmethyl]-2,3-dihydro-1H-indol-5-ol To (RS)-1-(5-methoxy-2,3-dihydro-1H-indol-2-ylmethyl)-4-(4-methyl-benzyl)-piperidin-4-ol (131 mg, 0.357 mol) in CH$_2$Cl$_2$ (10 ml) was added 1M BBr$_3$—CH$_2$Cl$_2$ (2.14 ml, 2.74 mmol, 6 eq.) at −78° C. over 5 min. The reaction was stirred at RT for 48 hr., then MeOH (20 ml) was added followed by 10% NaHCO$_3$ (20 ml), and the aqueous phase extracted with CH$_2$Cl$_2$ (2×50 ml) and the combined extracts washed with satd. NaCl solution (50 ml), dried over (Na$_2$SO$_4$) filtered and evaporated. Purification of the crude product over SiO$_2$ (Merck 230–400 mesh) eluting with CH$_2$Cl$_2$-MeOH (9:1) afforded (RS)-2-[4-hydroxy-4-(4-methyl-benzyl)-piperidin-1-ylmethyl]-2,3-dihydro-1H-indol-5-ol as a brown solid (64.6 mg, 0.183 mmol, 51%), Mp. 90–94° C., MS: m/e=353.3 (M+H$^+$).

Example 22

(RS)-N(2-[4-Chloro-4-(4-methyl-benzyl)-piperidin-1-ylmethyl]-2,3-dihydrobenzofuran-5-yl]-methane Sulfonamide Hydrochloride (RS)-N-(2-bromomethyl-2,3-dihydro-benzofuran-5-yl)-methansulfonamide (600 mg, 1.96 mmol), 4-(4-chloro-benzyl)-piperidin-4-ol (514 mg, 1.96 mmol), Et$_3$N(400 mg, 3.96 mmol) were dissolved in DMF (50 ml) and heated at 60° C. for 90 hrs. DMF was then evapored, the residue was dissolved in CH$_2$Cl$_2$ and washed with H$_2$O. The organic phase was dried over Na$_2$SO$_4$, and concentrated. The residue was chromatographed over SiO2 (Merck 230–400 mesh) eluting with $CH_2Cl_2$-MeOH-$NH_4OH$ (65:10:1) to provide a beige foam which was dissolved in THF (50 ml) and treated with 1.2N HCl (1 ml) to afford (RS)-N(2-[4-chloro-4-(4-methyl-benzyl)-piperidin-1-ylmethyl]-2,3-dihydrobenzofuran-5-yl]-methane sulfonamide hydrochloride as a white foam and mixture of E/Z isomers. MS: m/e=451.3 (M+H$^+$)

Following the Method of Example 22 the Compound of Example 23 was Prepared

Example 23

(RS)-N(2-[4-hydroxy-4-(4-methyl-benzyl)-piperidin-1-ylmethyl]-2,3-dihydrobenzofuran-5-yl-methane Sulfonamide Hydrochloride The title compound MS: m/e=431.5 (M+H$^+$) was prepared from (RS)-N-(2-bromomethyl-2,3-dihydro-benzofuran-5-yl)-methansulfonamide and 4-(4-Methyl-benzyl)-piperidin-4-ol.

Example 24

(RS)-1-(6-Hydroxy-2,3-dihydro-benzofuran-2-ylmethyl)-4-(4-methyl-benzyl)-piperidin-4-ol Hydrochloride (RS)-1-(6-methoxy-2,3-dihydro-benzofuran-2-ylmethyl)-4-(4-methyl-benzyl)-piperidin-4-ol (1.24g, 3.37 mmol) dissolved in 35 ml of $CH_2Cl_2$ was cooled to −8° C. and 1M $BBr_3$—$CH_2Cl_2$ solution (6.8 ml, 2 eq.) was added dropwise under argon. The violet suspension was allowed to warm to room temperature and then stirred for 30 minutes. The reaction was then cooled to 0° C. and MeOH (9 ml) was added to quench the reaction, followed by satd. $NaHCO_3$ (50 ml). The organic phase was separated and the aqueous phase was extracted with $CH_2Cl_2$ (2×50 ml). The combined organic extracts were dried with $Na_2SO_4$ then filtered and evaporated. The resulting yellow foam was chromatographed over $SiO_2$ (Merck 230–400 mesh) eluting with MeOH—$CH_2Cl_2$ (1:19) followed by MeOH—$CH_2Cl_2$ (1:9) to provide a yellow foam which was dissolved in MeOH (5 ml) and treated with 1N HCl (3.4 ml) to provide (RS)-1-(6-hydroxy-2,3-dihydro-benzofuran-2-ylmethyl)-4-(methyl-benzyl)-piperidin-4-ol hydrochloride (0.92g, 70%) as a white solid and mixture of E/Z isomers. Mp. 203–205° C. MS: m/e=354.3(M+H$^+$)

Following the Method of Example 24 the Compound of Example 25 was Prepared

Example 25

1-(6-Hydroxy-benzofuran-2-yl-methyl)-4-(4-methyl-benzyl)-piperidin-4-ol Hydrochloride The title compound m.p. 214° C. and MS: m/e=352.2 (M+H$^+$) was prepared from 1-(6-methoxy-benzofuran-2-ylmethyl)-4-(4-methyl-benzyl)-piperidin-4-ol.

Example 26

(RS)-4-Benzyl-1-(6-hydroxy-chroman-2-ylmethyl)-piperidin-4-ol Hydrochloride (RS)-4-Benzyl-1-(6-benzyloxy-chroman-2-ylmethyl)-piperidin-4-ol (0.58 g, 1.31 mmol) was dissolved in EtOAc (30 ml) and Pd/C 10% (135 mg) was added, the mixture was placed under an atmosphere of hydrogen and stirred vigorously for 17 hr at ambient temperature. Removal of the catalyst and chromatography over $SiO_2$ (Merck 230–400 mesh) $CH_2Cl_2$—MeOH—$NH_4OH$ (100:5:0.25) afforded a white foam (0.37 g, 1.04 mmol, 80%) which was taken up in EtOH (10 ml) and HCl/EtOH (1.1 eq.) was added at 0–5° C. Removal of the solvent gave (RS)-4-benzyl-1-(6-hydroxy-chroman-2-ylmethyl)-piperidin-4-ol hydrochloride (0.38 g, 0.98 mmol, 95%) a white foam, MS: m/e=354.4 (M+H$^+$).

Example 27

(1RS, 2RS)-(1-(1,6-Dihydroxy-1,2,34-tetrahydro-naphthalen-2-ylmethyl)-4-(4-methyl-benzyl)-piperidin-4-ol Fumarate Salt (1RS, 2RS) (1-(1,6-dihydroxy-1,2,3,4-tetrahydro-naphthalen-2-ylmethyl)-4-(4-methyl-benzyl)-piperidin-4-ol (0.581g, 1.53 mmol) in EtOH (20 ml) was stirred with fumaric acid (88 mg, 0.765 mmol, 0.5 eq) for 2 hr at RT. The mixture was then completely evaporated and dried under high vacuum to afford the title compound as an amorphous white foam (0.66g, quant.), MS:m/e=382.3 (M+H$^+$).

Example 28

(1RS, 2RS) (1-(1,6-Dihydroxy-1,23 4-tetrahydro-naphthalen-2-ylmethyl)-4-(4-methyl-benzyl)-piperidin-4-ol 1-(6-Benzyloxy-1-hydroxy-1,2,3,4-tetrahydro-naphthalen-2-ylmethyl)-4-(4-methyl-benzyl)-piperidin-4-ol (0.22 g, 0.46 mmol) in EtOAc (60 ml) was treated with Pd/C 10% (50 mg) and stirred for 6 hr at ambient temperature under an atmosphere of hydrogen. Removal of the catalyst and evaporation of the solvent afforded the title compound as a white foam (175 mg, quant.), MS m/e=382.3 (M+H$^+$).

Following the General Method of Example 28 Compound of Example 29 was Prepared

Example 29

(1RS,2RS)-2-(4-benzyl-4-hydroxy-piperidin-1-yl-methyl)-6-hydroxy-1,2,3,4-tetrahydro-naphthalen-1-ol The title compound was obtained as a white solid Mp. 94–98° C., MS: m/e=368.4 (M+H$^+$), prepared from (1RS, 2RS)-2-(4-benzyl-4-hydroxy-piperidin-1-yl-methyl)-6-benzyloxy-1,2,3,4-tetrahydro-naphthalen-1-ol.

Example 30

(RS)-1-(6-Hydroxy-1,2,3,4-tetrahydro-naphthalen-2-ylmethyl)-4-(4-methyl-benzyl)-piperidin-4-ol Hydrochloride To (RS)-1-(6-hydroxy-1,2,3 ,4-tetrahydro-naphthalen-2-ylmethyl)-4-(4-methyl-benzyl)-piperidin-4-ol (500 mg, 1.36 mmol) in EtOH (4 ml) at 4° C., was added ethanolic HCl (1.1 eq.). Evaporation of the EtOH afforded the title compound as a white foam (530 mg, 1.32 mmol, 97%), MS m/e=366.2 (M+H$^+$).

Example 31

(RS)-1-(6-Hydroxy-1,2,3,4-tetrahydro-naphthalen-2-ylmethyl)-4-(4-methyl-benzyl)-piperidin-4-ol To (RS)-1-(6-methoxy-1,2,3,4-tetrahydro-naphthalen-2-ylmethyl)-4-(4-methyl-benzyl)-piperidin-4-ol (843 mg, 2.22 mmol) in $CH_2Cl_2$ (20 ml) was added 1M $BBr_3$/$CH_2Cl_2$ (4.88 ml, 4.88 mmol, 2.2 eq.) over 15 min at −78° C., the mixture was then allowed to warm to RT over 40 min. MeOH (3 ml), $H_2O$ (20 ml) and $NaHCO_3$ (20 ml) were added and the mixture extracted with CH₂Cl₂ (4×50 ml). The extracts were washed with satd. NaCl solution (30 ml), dried (Na₂SO₄), filtered and evaporated, to afford the crude product as a yellow foam. Chromatography over SiO₂ (Merck 230–400 mesh) eluting with CH₂Cl₂—MeOH (97:3) afforded (RS)-1-(6-hydroxy-1,2,3,4-tetrahydro-naphthalen-2-ylmethyl)-4-(4-methyl-benzyl)-piperidin-4-ol as a white foam (500 mg, 13.68 mmol, 61%), MS m/e=366.2 (M+H⁺).

Example 32

(RS)-N-[6-(4-Benzyl-4-hydroxy-piperidin-1-ylmethyl)-5-oxo-5,6,7,8-tetrahydro-naphthalen-2-yl]-acetamide Hydrochloride N-(5,6,7,8-tetrahydro-5-oxo-2-naphthyl)acetamide (1.0 g, 4.92 mmol), 4-(benzyl)-piperidin-4-ol hydrochloride (1.12 g, 4.92 mmol) and paraformaldehyde (148 mg, 4.92 mmol) were heated together in DMF (50 ml) at 80° C. for 4 hr. The DMF was then evaporated and the residue taken up in CH₂Cl₂ (50 ml) and washed with 10% NaHCO₃ (25 ml), the aqueous phase was further extracted with CH₂Cl₂ (50 ml) and the combined CH₂Cl₂ extracts were dried (Na₂SO₄) filtered and evaporated. The crude material was chromatographed over SiO₂ (Merck 230–400 mesh) eluting with CH₂Cl₂—MeOH—NH₄OH (110:10:1) affording 0.79 g of a yellow foam. This material was dissolved in EtOH cooled to 0–4° C. and ethanolic HCl (1.1 eq.) added, the white solid which precipitated was collected and dried to afford (RS)-N-[6-(4-benzyl-4-hydroxy-piperidin-1-ylmethyl)-5-oxo-5, 6,7,8-tetrahydro-naphthalen-2-yl]-acetamide hydrochloride (639 mg, 1.44 mmol, 29%), Mp. 123–126° C., MS: m/e= 407.5 (M+H⁺).

N-(5,6,7,8-Tetrahydro-2-naphthyl)acetamide was prepared according to the literature:
Biggs, D. F. et al., *J. Med. Chem.*, 19, 1976, 472–475.;
Allinger, N. L.; Jones, E. S.,*J. Org. Chem.*, 27, 1962, 70–76.

PREPARATION OF INTERMEDIATES
General Preparation of Benzyl Piperidin Intermediates

Example 33

(RS)-1-(5-Benzyloxy-2,3-dihydro-benzofuran-2-ylmethyl)-4-(4-methyl-benzyl)-piperidin-4-ol (RS)-5-Benzyloxy-2-bromomethyl-2,3-dihydro-benzofuran (840 mg, 2.63 mmol) and 4-(4-methyl-benzyl)-piperidin-4-ol (1.08 g, 5.26 mmol) were suspended in toluene (20 ml) and heated to 110° C. for 17 hr. The mixture was filtered and evaporated to afford an orange oil which was chromatographed over SiO₂ (Merck 230–400 mesh) with MeOH—CH₂Cl₂ (3:97) to afford (RS)-1-(5-benzyloxy-2,3-dihydro-benzofuran-2-ylmethyl)-4-(4-methyl-benzyl)-piperidin-4-ol as a yellow oil (1.03 g, 2.32 mmol, 88%), MS: m/e=444.5 (M+H⁺).

PREPARATION OF INTERMEDIATES FOR EXAMPLES 2–12

Following the General Method of Example 33. Examples 34 to 43 were Prepared

Example 34

1-(5-Benzyloxy-2,3-dihydro-benzofuran-2-ylmethyl)-4-(4-methoxy-benzyl)-piperidin-4-ol The title compound MS: m/e=460.2 (M+H⁺) was prepared from 4-(4-methoxy-benzyl)-piperidin-4-ol and 5-benzyloxy-2-(RS)-bromomethyl-2,3-dihydro-benzofuran.

Example 35

(RS)-4-Benzyl-1-(5-benzyloxy-2,3-dihydro-benzofuran-2-ylmethyl)-piperidin-4-ol

The title compound MS: m/e=430.6 (M+H⁺) was prepared from 4-(benzyl)-piperidin-4-ol and 5-benzyloxy-2-(RS)-bromomethyl-2,3-dihydro-benzofuran.

Example 36

(RS)-4-(4-Fluoro-benzyl)-1-(5-benzyloxy-2 3-dihydro-benzofuran-2-ylmethyl)-piperidin-4-ol The title compound MS: m/e=448.6 (M+H⁺) was prepared from 4-(4-fluoro-benzyl)-piperidin-4-ol and 5-benzyloxy-2-(RS)-bromomethyl-2,3-dihydro-benzofuran.

Example 37

(RS)-4-(3,4-Dimethyl-benzyl)-1-(5-benzyloxy-2,3-dihydro-benzofuran-2-ylmethyl)-piperidin-4-ol The title compound MS: m/e=458.6 (M+H⁺) was prepared from 4-(3,4-dimethyl-benzyl)-piperidin-4-ol and 5-benzyloxy-2-(RS)-bromomethyl-2,3-dihydro-benzofuran.

Example 38

(RS)-4-(4-Ethyl-benzyl)-1-(5-benzyloxy-2,3-dihydro-benzofuran-2-ylmethyl)-piperidin-4-ol The title compound MS: m/e=458.6 (M+H⁺) was prepared from 4-(4-ethyl-benzyl)-piperidin-4-ol and 5-benzyloxy-2-(RS)-bromomethyl-2,3-dihydro-benzofuran.

Example 39

(RS)-4-(4-Isopropyl-benzyl)-1-(5-benzyloxy-2,3-dihydro-benzofuran-2-ylmethyl)-piperidin-4-ol The title compound MS: m/e=472.6 (M+H⁺) was prepared from 4-(4-isopropyl-benzyl)-piperidin-4-ol and 5-benzyloxy-2-(RS)-bromomethyl-2,3-dihydro-benzofuran.

Example 40

(RS)-4-(2-Methyl-benzyl)-1-(5-benzyloxy-2,3-dihydro-benzofuran-2-ylmethyl)-piperidin-4-ol The title compound MS: m/e=444.6 (M+H⁺) was prepared from 4-(2-methyl-benzyl)-piperidin-4-ol and 5-benzyloxy-2-(RS)-bromomethyl-2,3-dihydro-benzofuran.

Example 41

(RS)-4-(2,4-Difluoro-benzyl)-1-(5-benzyloxy-2,3-dihydro-benzofuran-2-ylmethyl)-piperidin-4-ol The title compound MS: m/e=466.6 (M+H⁺) was prepared from 4-(2,4-difluoro-benzyl)-piperidin-4-ol and 5-benzyloxy-2-(RS)-bromomethyl-2,3-dihydro-benzofuran.

Example 42

(RS)-4-(4-Trifluoromethoxy-benzyl)-1-(5-benzyloxy-2,3-dihydro-benzofuran-2-ylmethyl)-piperidin-4-ol The title compound MS: m/e=514.6 (M+H⁺) was prepared from 4-(4-trifluoromethoxy-benzyl)-piperidin-4-ol and 5-benzyloxy-2-(RS)-bromomethyl-2,3-dihydro-benzofuran.

Example 43

(RS)-4-(3-Trifluoromethyl-benzyl)-1-(5-benzyloxy-2,3-dihydro-benzofuran-2-ylmethyl)-piperidin-4-ol The title compound MS: m/e=498.6 (M+H⁺) was prepared from 4-(3-trifluoromethyl-benzyl)-piperidin-4-ol and 5-benzyloxy-2-(RS)-bromomethyl-2,3-dihydro-benzofuran.

Example 44

(RS)-5-Benzyloxy-2-(bromomethyl-2,3-dihydro-benzofuran (RS)-Acetic acid 4-benzyloxy-2-(2,3-dibromo-propyl)-phenyl ester (5.05 g, 11.3 mmol) was suspended in EtOH (50 ml) and sodium methoxide (620 mg, 11.3 mmol) added and the mixture stirred for 2 hr at ambient temperature. Distilled $H_2O$ (100 ml) and $CH_2Cl_2$ (100 ml) was then added and the organic phase separated. The aqueous phase was extracted with $CH_2Cl_2$ (100 ml) and the combined organic extracts washed with satd. NaCl solution (100 ml). After drying with $Na_2SO_4$, filtration and evaporation a yellow oil resulted which was chomatographed over $SiO_2$ (Merck 230–400 mesh) with $CH_2Cl_2$ to afford 5-benzyloxy-2-(RS)-bromomethyl-2,3-dihydro-benzofuran as a yellow oil (3.0 g, 9.39 mmol, 83%), MS: m/e=318.0 ($M^+$).

Example 45

(RS)-Acetic acid 4-benzyloxy-2-(2,3-dibromo-propyl)-phenyl Ester

To a solution of acetic acid-2-allyl-4-benzyloxy-phenyl ester (3.30 g, 11.7 mmol) in $CCl_4$ (30 ml) at 0–5° C., bromine (0.6 ml, 11.7 mmol) was added over 10 min. and the resulting mixture stirred for 1 hr at 5–10° C. $Na_2CO_3$ solution (10%, 4 ml) and distilled $H_2O$ (10 ml) were added to quench the reaction. The organic phase was separated, dried with $Na_2SO_4$ and then evaporated to afford a colourless oil, which crystallised to provide on standing (RS)-acetic acid 4-benzyloxy-2-(2,3-dibromo-propyl)-phenyl ester (5.05 g, 11.4 mmol, 97%), Mp. 72–74° C., MS: m/e=440.0 ($M^+$).

Example 46

Acetic acid-2-allyl-4-benzyloxy-phenyl Ester

2-Allyl-4-benzyloxy-phenol (2.87 g, 12 mmol) was taken up in acetic anhydride (40 ml) and NaOAc (150 mg, 1.8 mmol) was added and the mixture heated 18 hr at 80° C. After cooling, the reaction mixture was evaporated to afford an oil which was partitioned between EtOAc and $H_2O$ (100 ml) and the aqueous phase was extracted with EtOAc (100 ml) and the combined organic phases were dried with $MgSO_4$, filtered and evaporated to afford acetic acid- 2-allyl-4-benzyloxy-phenyl ester as a pale yellow oil (3.30 g, 11.7 mmol, 97%), MS: m/e=282.1 ($M^+$).

Example 47

2-Allyl-4-benzyloxy-phenol

1-Benzyloxy-4-allyloxy-benzene (20.4 g, 84.9 mmol) dissolved in mesitylene (150 ml) was heated at 165° C. for 48 hr under an argon atmosphere. After cooling to ambient temperature the resulting brown oil was chromatographed over $SiO_2$ (Merck 230–400 mesh) eluting with EtOAc-nHexane (1:9) to afford 2-allyl-4-benzyloxy-phenol (17.45 g, 72.6 mmol, 85%) as a pale yellow oil MS m/e=240.1 ($M^+$).

Example 48

1-Benzyloxy-4-allyloxy-benzene

4-Benzyloxyphenol (20 g, 100 mol), $K_2CO_3$ (20.8 g, 150 mmol) and allyl bromide (12.7 ml, 150 mmol) were heated under reflux in acetone (200 ml) 18 hr. After filtration and evaporation of the solvent 1-benzyloxy-4-allyloxy-benzene (23.8 g, 99 mmol, 99%) was afforded as a beige solid Mp. 56–57° C., MS m/e=240.1 ($M^+$).

PREPARATION OF THE INTERMEDIATES FOR EXAMPLES 13 AND 14

Example 49

(S)-1-(5-Methoxy-2 3-dihydro-benzofuran-2-ylmethyl)-4-(4-methyl-benzyl)-piperidin-4-ol (S)-Toluenesulfonic acid 5-methoxy-2,3-dihydro-benzofuran-2-ylmethyl ester (2.30g, 6.88 mmol) and 4-(4-methyl-benzyl)-piperidin-4-ol (1.62 g, 7.9 mmol) and $Na_2CO_3$ (1.10 g, 10.3 mmol) were suspended in DMF and heated at 110° C. for 1 hr. After cooling to ambient temperature distilled $H_2O$ and EtOAc were added (100 ml) and the mixture shaken, the organic phase was then separated and the aqueous phase extracted with EtOAc (10 ml). The combined organic extracts were then washed with satd. NaCl solution (100 ml) and the organic phase dried with $Na_2SO4$, filtered and evaporated to afford a yellow oil. This foam was chromatographed over $SiO_2$ (Merck 230–400 mesh) with $CH_2Cl_2$, and then with $CH_2Cl_2$—MeOH (97:3) to afford (S)-1-(5-methoxy-2,3-dihydro-benzofuran-2-ylmethyl)-4-(4-methyl-benzyl)-piperidin-4-ol (2.20 g, 6.0 mmol, 87% yield) as a yellow oil MS: m/e=368.2 ($M+H^+$) $[\alpha]$=+45.8° (c=1.0, $CHCl_3$).

Following the General Method of Example 49, Example 50 was Prepared

Example 50

(S)-1-(5-Methoxy-2,3-dihydro-benzofuran-2-ylmethyl)-4-(4-chloro-benzyl)-piperidin-4-ol The title compound, MS: m/e=387.9 ($M+H^+$), was prepared from 4-(4-chloro-benzyl)-piperidin-4-ol and (S)-toluenesulfonic acid 5-methoxy-2,3-dihydro-benzofuran-2-ylmethyl ester.

Example 51

(S)-Toluenesulfonic acid 5-methoxy-2,3-dihydro-benzofuran-2-ylmethyl Ester

A solution of (S)-5-methoxy-2,3-dihydro-benzofuran-2-carboxylic acid (2.4 g, 12.4 mmol) in THF (30 ml) was added dropwise to a suspension of $LiAlH_4$ (0.71 g, 18.5 mmol) in THF (20 ml) over 15 min with cooling. The mixture was then heated to reflux for 1 hr., after cooling distilled $H_2O$ (0.7 ml) was added followed by 4N NaOH (1.4 ml) and distilled $H_2O$ (2.1 ml). The whole mixture was dried with $Na_2SO_4$, filtered and evaporated to afford a light yellow oil (2.20 g, 12.2 mmol, 100%). This oil was dissolved in pyridine (22 ml) and p-toluene sulfonyl chloride was added (3.48 g, 18.3 mmol), and the mixture stirred at ambient temperature for 1 hr. $H_2O$ was then added to the crude mixture and vigorously stirrred for 10 min., extraction with EtOAc (2×100 ml) and washing the organic phase with 2N HCl (150 ml) followed by satd. NaCl (100 ml), drying with $Na_2SO_4$ and evaporation afforded a yellow oil. This oil was chromatographed over $SiO_2$ (Merck 230–400 mesh) with cyclohexane-EtOAc (4:1) to afford (S)-toluenesulfonic acid 5-methoxy-2,3-dihydro-benzofuran-2-ylmethyl ester (2.4g 7.2 mmol, 57%) as a white solid Mp. 82–84° C., MS: m/e=334.1 ($M^+$) $[\alpha]$=+75.1° (c=1.0, $CHCl_3$).

Example 52

(S)-5-Methoxy-2,3-dihydro-benzofuran-2-carboxylic acid

To a solution of R(+)-1-(1-naphthyl)ethylamin (3.80 g, 22.2 mmol) in acetone (40 ml) was added (RS)-5-methoxy- 2,3-dihydro-benzofuran-2-carboxylic acid (4.1 g, 21.1 mmol) in acetone (80 ml) after 2–3 min. stirring at ambient temperature a beige solid precipitated, the mixture was cooled to 0–5° C. and stirred for a further 30 min. The solid was filtered and washed with cold (4° C.) acetone (3×20 ml) to afford white crystals 6 g, Mp. 183–190° C. This solid was recrystallised twice from hot EtOH (60 ml) to afford 4.0 g of white crystals Mp. 190–194° C. This material was suspended in EtOAc (100 ml) and washed with 1N HCl (50 ml), the acidic aqueous phase was extracted with EtOAc (50 ml), the combined organic extracts were then washed with distilled $H_2O$ (50 ml) and then dried with $Na_2SO_4$ and evaporated to afford (S)-5-methoxy-2,3-dihydro-benzofuran-2-carboxylic acid (2.3 g, 11.8 mmol, 77%) as a pale yellow crystalline solid Mp. 85–87° C., MS: m/e=194.2 ($M^+$) [α]=−9.2° (c=1.0, EtOH).

Example 53

(RS)-5-Methoxy-2,3-dihydro-benzofuran-2-carboxylic acid

To a suspension of 5-methoxy-benzofuran-2-carboxylic acid (14 g, 72.8 mmol) in MeOH (600 ml) was added magnesium turnings (10.6 g, 437 mmol) and the mixture was vigorously mechanically stirred for 2 hr keeping the temperature below 30° C. After 2 hr, further magnesium was added (10.6 g, 437 mmol) and the mixture stirred a further 4 hr again maintaining the temperature below 30° C. After 6 hr. the mixture was concentrated to ~100 ml and distilled $H_2O$ (600 ml) was added and the pH adjusted to 1–2 with 1N sulfuric acid. The crude mixture was extracted with EtOAc (2×300 ml) and the combined extracts washed with $H_2O$ (200 ml). The combined organic phase was dried with $Na_2SO_4$, filtered and evaporated to afford yellowish solid, which was recrystallised from hot toluene (100 ml) to afford white crystals (9.2 g, 47.4 mmol, 65%) Mp. 98–100° C., MS: m/e=194.1 ($M^+$).
Following the General Method of Example 49 Compound of Example 54 was Prepared Example 54

(R)-1-(5-Methoxy-2,3-dihydro-benzofuran-2-ylmethyl)-4-(4-methyl-benzyl)-piperidin-4-ol The title compound (2.40 g, 6.53 mmol, 76% yield) as a yellow oil MS: m/e=368.2 ($M+H^+$) [α]=−44.0° (c=1.0, $CHCl_3$) was prepared from (R)-toluenesulfonic acid 5-methoxy-2,3-dihydro-benzofuran-2-ylmethyl ester.
Following the General Method of Example 51 Compound of Example 55 was Prepared Example 55

(R)-Toluenesulfonic acid 5-methoxy-2,3-dihydro-benzofuran-2-ylmethyl Ester

The title compound (3.0 g 9.0 mmol, 67%) as a white solid Mp. 82–84° C., MS: m/e=334.1 ($M^+$) [α]=−74.9° (c=1.0, $CHCl_3$) >99% e.e. by chiral phase HPLC was prepared from (R)-5-methoxy-2,3-dihydro-benzofuran-2-carboxylic acid.

Example 56

(R)-5-Methoxy-2,3-dihydro-benzofuran-2(R)-carboxylic Acid

To a solution of S(−)-1-(1-naphthyl)ethylamin (7.21g, 41.6 mmol) in acetone (80 ml) was added (RS)-5-methoxy-2,3-dihydro-benzofuran-2-carboxylic acid (7.70 g, 39.6 mmol) in acetone (150 ml) after 2–3 min. stirring at ambient temperature a beige solid precipitated, the mixture was cooled to 0–5° C. and stirred for a further 30 min. The solid was filtered and washed with cold (4° C.) acetone (3×20 ml) to afford white crystals 9.90 g, Mp.145–160° C. This solid was recrystallised twice from hot EtOH (125 ml) to afford 4.75 g of white crystals Mp. 185–194° C. This material was suspended in EtOAc (100 ml) and washed with iN HCl (50 ml), the acidic aqueous phase was extracted with EtOAc (50 ml), the combined organic extracts were then washed with distilled $H_2O$ (50 ml) and then dried with $Na_2SO_4$ and evaporated to afford (R)-5-methoxy-2,3-dihydro-benzofuran- 2-carboxylic acid (2.5 g, 12.9 mmol, 65%) as a pale yellow crystalline solid Mp. 85–87° C., MS: m/e=194.1 ($M^+$) [α]=+9.8° (c=1.0, EtOH).

Example 57

Mixture of (1RS,2RS) and (1RS 2SR)-2-[4-benzyloxy-4-(4-methyl-benzyl)-piperidine-1-ylmethyl]-indan-1,5-diol 5-Benzyloxy-indan-1-one (2.38 g, 10 mmol), 4-(4-methyl-benzyl)-piperidin-4-ol hydrochloride (2.41 g, 10 mmol) and paraformaldehyde (0.3 g, 10 mmol) in DMF (20 ml) were heated at 70° C. for 20 hr. After cooling EtOAc (150 ml), distilled $H_2O$ (200 ml) and 25% $NH_4OH$ (4 ml) was added and the mixture shaken. The aqueous phase was further extracted with EtOAc (150 ml) and the combined organic extracts were washed with satd. NaCl (2×100 ml) and dried with $Na_2SO_4$, affording a yellow oil after evaporation. This oil was dissolved in TTIF (40 ml) and added over 30 min to a suspension of $LiAlH_4$ (1.87 g, 50 mmol, 5 eq.) in THF (50 ml) with ice cooling (5–15° C.). The mixture was then allowed to stir for a further 2 hr at RT, the reaction was quenched by the addition of distilled $H_2O$ (2 ml), 4N NaOH (4 ml) then $H_2O$ (4 ml) and stirred for 15 min vigorously. The whole mixture was then dried with $Na_2SO_4$, filtered, washed with THF and evaporated to afford a viscose oil. The crude product was chromatographed over $SiO_2$ (Merck 230–400 mesh) eluting with $CH_2Cl_2$—MeOH (97:3) then $CH_2Cl_2$—MeOH (9:1) to afford a white foam which could be crystallised from EtOAc-$Et_2O$ affording (1RS,2RS) and (1RS, 2SR)-2-[4-benzyloxy-4-(4-methyl-benzyl)-piperidine-1-ylmethyl]-indan-1,5-diol as white crystals (1.89 g, 4.13 mmol, 41%), Mp. 131–132° C., MS m/e=458.4 ($M+H^+$).

Example 58

5-Benzyloxy-indan-1-one

A mixture of 5-hydroxy-indan-1-one (5.3 g, 35.7 mmol), KJ (0.6 g, 3.6 mmol) and $K_2CO_3$ (6.17 g, 44.6 mmol) and benzyl bromide (4.66 ml, 39.3 mmol) in DMF (50 ml) were heated at 100° C. for 1 hr. Addition of $H_2O$ (150 ml) and extraction with EtOAc (3×50 ml), washing the organic phase with satd. NaCl solution (100 ml) and drying with $MgSO_4$ and evaporation afforded a brown solid. This material was recrystallised twice from EtOH to afford 5-benzyloxy-indan-1-one (6 g, 25.17 mmol, 70%) as yellow crystals, Mp. 105–106° C., MS m/e=238.1 ($M^+$).

Example 59

5-Hydroxy-indan-1-one

5-Methoxy-indan-1-one (8 g, 49.3 mmol), and 4-tert-butyl-2-methyl-benzenethiol sodium salt (11.92 g, 59.2 mmol) were heated at 142° C. for 1 hr under argon. After cooling to RT, water (80 ml) was added followed by 1N HCl (80 ml) and EtOAc (120 ml). The mixture was shaken and the aqueous phase extracted with EtOAc (100 ml), the combined organic extracts were washed with satd.NaCl solution (100 ml) and dried with $Na_2SO_4$, filtered and evaporated. The residue was chomatographed over $SiO_2$ (Merck 230–400 mesh) eluting with EtOAc-nHexane (2:3), producing 5-hydroxy-indan-1-one (3.55g, 22.6 mmol, 45.9 %) as orange crystals Mp. 185–187° C., MS m/e=148.2 ($M^+$).

Example 60

(RS)-1-(5-Methoxy-2,3-dihydro-1H-indol-2-ylmethyl)-4-(4-methyl-benzyl)-piperidin-4-ol To a solution of (RS)-1-[5-methoxy-1-(toluene-4-sulfonyl)-2,3-dihydro-1H-indol-2-ylmethyl]-4-(4-methyl-benzyl)-piperidin-4-ol (300 mg, 0.576 mmol) in toluene (15 ml) was added sodium bis(2-methoxy-ethoxy) aluminium hydride (3.5 M in THF) (0.66 ml, 2.31 mmol), and the mixture refluxed 18 hr. After cooling, 2N NaOH was added to pH 14, the mixture was extracted with EtOAc (3x 25ml) and the combined extracts washed with satd. NaCl (25 ml), dried with ($Na_2SO_4$) then filtered and evaporated. The residue was chromatographed over $SiO_2$ (Merck 230–400 mesh) eluting with EtOAc-cyclohexane-$Et_3N$ (9:10:1) to afford (RS)-1-(5-methoxy-2,3-dihydro-1H-indol-2-ylmethyl)-4-(4-methyl-benzyl)-piperidin-4-ol as a viscous yellow oil (158.4 mg, 0.433 mmol, 75%), MS: m/e=367.3 ($M+H^+$).

Example 61

(RS)-1-[5-Methoxy-1-(toluene-4-sulfonyl)-2,3-dihydro-1H-indol-2-ylmethyl]-4-(4-methyl-benzyl)-piperidin-4-ol (RS)-Toluene-4-sulfonic acid 5-methoxy-1-(toluene-4-sulfonyl)-2,3-dihydro-1H-indol-2-ylmethyl ester (200 mg, 0.41 mmol) and 4-(4-methylbenzyl)-piperidin-4-ol (337 mg, 1.64 mmol) were heated in mesitylene (10 ml) for 20 hr at 140° C. After cooling 4N HCl was added to pHl and the mixture extracted with EtOAc (3×25 ml), the extracts dried ($Na_2SO_4$), filtered and evaporated. Purification of the crude material over $SiO_2$ (Merck 230–400 mesh) eluting with EtOAc-cyclohexane-$Et_3N$ (9:10:1) afforded the title compound as a yellow oil (155.9 mg, 0.3 mmol, 73%), MS: m/e=521.4 ($M+H^+$).

Example 62

(RS)-Toluene-4-sulfonic acid 5-methoxy-1-(toluene-4-sulfonyl)-2,3-dihydro-1H-indol-2-ylmethyl Ester (RS)-(5-methoxy-2,3-dihydro-1H-indol-2-yl)-methanol (100 mg, 0.46 mmol), p-toluenesulfonyl chloride (177 mg, 0.93 mmol), triethylamine (0.21 ml, 1.48 mmol) and N,N-dimethylamino pyridine (2 mg) were stirred for 18 hr at RT in $CH_2Cl_2$ (5 ml). 1N HCl (10 ml) was added, the mixture extracted with $CH_2Cl_2$ (2×25 ml) and the extracts washed with satd. NaCl solution (20 ml) and dried ($Na_2SO_4$). The crude material was chromatographed over $SiO_2$ (Merck 230–400 mesh) eluting with EtOAc-cyclohexane-$Et_3N$ (9:10:1) to afford the title compound as a yellow oil (172.8 mg, 0.35 mmol, 76%), MS: m/e=488.0 ($M+H^+$).

Example 63

(RS)-(5-Methoxy-2,3-dihydro-1H-indol-2-yl)-methanol (RS)-5-methoxy-2,3-dihydro-1H-indole-2-carboxylic acid methyl ester (2.5 g, 12.06 mmol) in THF (130 ml) was added dropwise to a suspension of $LiAlH_4$ in THF (80 ml) at 4° C., and the mixture allowed to stir at RT overnight, and then heated at 65° C. for 4 hr. After cooling, $H_2O$ (20 ml) was added cautiously and the mixture stirred 20 min, then filtered and the filtrate extracted with EtOAc (3×50 ml), the extracts were washed with satd. NaCl solution (50 ml), dried ($Na_2SO_4$) filtered and evaporated. The crude oil was chromatographed over $SiO_2$ (Merck 230–400 mesh) eluting with $CH_2Cl_2$—MeOH (9:1) affording (RS)-(5-methoxy-2,3-dihydro-1H-indol-2-yl)-methanol as a yellow oil (1.41 g, 7.86 mmol, 65%), MS: m/e=179.1 ($M^+$).

Example 64

(RS)-5-Methoxy-2,3-dihydro-1H-indole-2-carboxylic Acid Methyl Ester

To 5-methoxy-1H-indole-2-carboxylic acid ethyl ester (5 g, 22.8 mmol) in MeOH (150 ml) was added magnesium turnings (2.2 g, 91.6 mmol, 4eq.) and the mixture vigorously mechanically stirred (10–30° C.) for 2 hr. 4N HCl was added (to pH1–2), then 25% $NH_4OH$ (to pH 7), and the mixture extracted with EtOAc (4×100 ml). The combined extracts were then washed with satd. NaCl solution (50 ml), dried ($Na_2SO_4$) filtered and evaporated. The crude green oil was chromatographed over $SiO_2$ (Merck 230–400 mesh) eluting with EtOAc-nHexane (1:3) to afford the title compound (3.21g, 15.5 mmol, 68%) as a yellow solid Mp. 59–61° C., MS: m/e=207.1 ($M^+$).

Example 65

5-Methoxy-1H-indole-2-carboxylic Acid Ethyl Ester

5-Methoxy-1H-indole-2-carboxylic acid (10 g, 52.3 mmol) in EtOH (400 ml) containing 36% $H_2SO_4$ (7 ml) was heated under reflux for 18 hr. After cooling the mixture was neutralised with 2N NaOH (to pH 7) and extracted with EtOAc (3×150ml), the combined extracts were washed with 10% $NaHCO_3$ (2×25 ml), dried ($MgSO_4$), filtered and evaporated to afford 5-methoxy-1H-indole-2-carboxylic acid ethyl ester as a brown solid (9.52 g, 43.3 mmol, 82%) Mp. 154–155° C., MS: m/e=219.1 ($M^+$).

PREPARATION OF THE INTERMEDIATES FOR EXAMPLES 22 AND 23

Example 66

(RS)-N-(2-Bromomethyl-2,3-dihydro-benzofuran-5-yl)-methansulfonamide (RS)-2-bromomethyl-2,3-dihydro-benzofuran-5-ylamine (410 mg, 1.80 mmol), methansulfonyl-chloride (206 mg, 1.8 mmol), $Et_3N$ (182 mg, 1.80 mmol) were dissolved in $CH_2Cl_2$ (50 ml) and stirred overnight at room temperature. Solvent was then evaporated and the residue was chromatographed over $SiO_2$ (Merck 230–400 mesh) eluting with $CH_2Cl_2$—MeOH (95:5) to provide (RS)-N-(2-bromomethyl-2,3-dihydro-benzofuran-5-yl)-methansulfonamide (516 mg, 94%) as an oil. MS: m/e= 305.9 ($M-H^+$)

(RS)-2-bromomethyl-2,3-dihydro-benzofuran-5-ylamine was prepared following the procedure described in example 44.

PREPARATION OF THE INTERMEDIATES FOR EXAMPLES 24 AND 25

Example 67

(RS)-1-(6-Methoxy-2,3-dihydro-benzofuran-2-ylmethyl)-4-(4-methyl-benzyl)-piperidin-4-ol (RS)-toluene-4-sulfonic acid 6-methoxy-2,3-dihydro-benzofuran-2-ylmethyl ester (110 mg, 0.33 mmol) and 4-(4- methyl-benzyl)-piperidin-4-ol (148 mg, 0.72 mmol) were dissolved in DMF (3 ml) and heated at 130° C. for 1 h. DMF was then evaporated, the residue was dissolved in $CH_2Cl_2$ (5 ml) and washed with $H_2O$ (5 ml). Organic phase was dried over $Na_2SO_4$, and concentrated. The residue was chromatographed over $SiO_2$ (Merck 230–400 mesh) eluting with $CH_2Cl_2$-MeOH(19:1) to provide (RS)-1-(6-methoxy-2,3-dihydro-benzofuran-2-ylmethyl)-4-(4-methyl-benzyl)-piperidin-4-ol (80 mg, 66%) as a yellow oil, MS:m/e=368.4 $(M+H^+)$.

Example 68

(RS)-Toluene-4-sulfonic acid 6-methoxy-2,3-dihydro-benzofuran-2-ylmethyl Ester

To a solution of (RS)-(6-methoxy-2,3-dihydro-benzofuran-2-yl)-methanol (0.09 g, 0.5 mmol), $Et_3N$ (0.1 ml, 0.75 mmol), DMAP (1 mg, 0.01 mmol) in $CH_2Cl_2$ (1.5 ml) at 0° C. was added dropwise a solution of p—toluenesulfonylchloride (115 mg, 0.6 mmol). The reaction mixture was allowed to warm to room temperature and was stirred during 4 hr before the addition of $H_2O$ (2 ml). The aqueous phase was extracted with $CH_2Cl_2$ (2×5 ml). Combined organic phases were dried over $Na_2SO_4$, and concentrated. The residue was chromatographed over $SiO_2$ (Merck 230–400 mesh) eluting with nHexane-EtOAc (4:1) to provide (RS)-toluene-4-sulfonic acid 6-methoxy-2,3-dihydro-benzofuran-2-ylmethyl ester (120 mg, 72%) as a colorless oil, MS:m/e=334 $(M^+)$.

Example 69

1-(6-Methoxy-benzofuran-2-ylmethyl)-4-(4-methyl-benzyl)-piperidin-4-ol

To a solution of 6-methoxy-2-benzofuranmethanol (89 mg, 0.5 mmol) in dioxan (3 ml) at room temperature was added dropwise $SOCl_2$ (0.11 ml, 1.5 mmol). After 1.5 hr, the reaction mixture was concentrated at room temperature under high vacuum. The residue was dissolved in dioxan (3 ml) and treated with 4-(4-methyl-benzyl)-piperidin-4-ol (225 mg, 1.1 mmol). After stirring 17 hr at room temperature, the solvent was evaporated. The residue was taken up in $H_2O$ (4 ml) and extracted with $CH_2Cl_2$ (6×4 ml). The combined organic phases were dried over $Na_2SO_4$, and concentrated. The residue was chromatographed over $SiO_2$ (Merck 230–400 mesh) eluting with $CH_2Cl_2$—MeOH (19:1) to provide 1-(6-methoxy-benzofuran-2-ylmethyl)-4-(4-methyl-benzyl)-piperidin-4-ol (140 mg, 77%) as a yellow oil, MS:m/e=366.3 $(M+H_-^+)$.

Example 70

(RS)-(6-Methoxy-2,3-dihydro-benzofuran-2-yl)-methanol

A solution of (RS)-6-methoxy-2,3-dihydro-benzofuran-2-carboxylic acid (158 mg, 0.813 mmol) in THF (2 ml) was added dropwise in a 0° C. suspension of $LiAlH_4$ (31 mg, 0.813 mmol) in THF (2 ml). After 30 min stirring at 0° C., the reaction mixture was allowed to reflux for 30 minutes. The reaction mixture was then cooled to 0° C. and treated successively with $H_2O$ (0.05 ml), 5N NaOH (0.05 ml), $H_2O$ (0.15 ml). After 20 minutes stirring at room temperature, EtOAc was added followed by $Na_2SO_4$. The so obtained solid was filtered and the filtrate was evaporated. The residue was chromatographed over $SiO_2$ (Merck 230–400 mesh) eluting with nHexane-EtOAc (4:1) to provide (RS)-(6-methoxy-2,3-dihydro-benzofuran-2-yl)-methanol (102 mg, 70%) as a colorless oil, MS:m/e=180 $(M^+)$.

Following the Method of Example 70 the Compound of Example 71 was Prepared

Example 71

6-Methoxy-2-benzofuranmethanol

The title compound MS: m/e=178 (M+) was prepared from 6-methoxy-2-enzofurancarboxylic acid.

Following the Method of Example 53 the Compound of Example 72 was Prepared

Example 72

(RS)-6-Methoxy-2,3-dihydro-benzofuran-2-carboxylic Acid

The title compound Mp. 108–110° C. MS: m/e=194 $(M^+)$ was prepared from 6-methoxy-2-benzofurancarboxylic acid.

6-Methoxy-2-benzofurancarboxylic acid was prepared according to the literature:

S. Tanaka, *J. Am. Chem. Soc.* 73, 1951, 872

Example 73

(RS)-4-Benzyl-1-(6-benzyloxy-chroman-2-ylmethyl)-piperidin-4-ol (RS)-6-Benzyloxy-2-bromomethyl-chroman (0.52 g, 1.56 mmol) and 4-(benzyl)-piperidin-4-ol (0.66 g, 3.43 mmol) in toluene (20 ml) was refluxed for 18 hr under argon. After removal of the solvent the crude mixture was chromatographed over $SiO_2$ (Merck 230–400 mesh) $CH_2Cl_2$—MeOH—$NH_4OH$ (100:5:0.25) to afford the title compound (RS)-4-benzyl-1-(6-benzyloxy-chroman-2-ylmethyl)-piperidin-4-ol as a yellow oil (0.6 g, 1.35 mmol, 86%), MS: m/e=444.5 $(M+H^+)$.

Example 74

(RS)-6-Benzyloxy-2-bromomethyl-chroman (RS)-6-Benzyloxy-(chroman-2-yl)-methanol (0.97 g, 3.58 mmol) and 1,1'-carbonyldiimidazole (0.58 g, 3.58 mmol) and allyl bromide (19.9 mmol) were heated in acetonitrile at 80° C. for 4 hr. The crude mixture was then evaporated to dryness and chomatographed over $SiO_2$ (Merck 230–400 mesh) eluting with $CH_2Cl_2$. This afforded (RS)-6-benzyloxy-2-bromomethyl-chroman (0.28 g, 0.84 mmol, 23%) as a white solid Mp. 61–63° C., MS m/e=332.0 $(M^+)$.

Example 75

(RS)-6-Benzyloxy-(chroman-2-yl)-methanol

To a stirred suspension of $LiAlH_4$ (0.352 g, 9.26 mmol) in THF at 10° C. was added a solution of (RS)-6-hydroxy-chroman-2-carboxylic acid (1.2 g, 6.18 mmol) in THF (25 ml) over 15 min. After allowing to warm to ambient temperature, 4N HCl (25 ml) and EtOAc (100 ml) was added and the mixture shaken. The aqueous phase was extracted with EtOAc (100 ml) and the combined organic extracts were washed with satd. NaCl (50 ml), dried with $Na_2SO_4$ and evaporated. The resulting solid was taken up in acetone (50 ml) then $K_2CO_3$ (0.94 g, 6.8 mmol) and benzyl bromide (0.81 ml, 6.8 mmol) were added and the mixture refluxed for 18 hr. The reaction mixture was filtered, evaporated to dryness and chromatographed over $SiO_2$ (Merck 230–400 mesh) eluting with EtOAc-cyclohexane (3:7) to afford (RS)-6-benzyloxy-(chroman-2-yl)-methanol (1.0 g, 3.7 mmol, 60%) as a white solid Mp. 80–82° C., MS mn/e=270.1 $(M^+)$.

Example 76

(RS)-6-Hydroxy-chroman-2-carboxylic Acid (RS)-6-Methoxy-chroman-2-carboxylic acid (1.12 g, 5.37 mmol) and pyridinium hydrochloride (11.2 g, 96.6 mmol)

were heated together at 180° C. for 2 hr under argon with stirring. After cooling to ambient temperature H$_2$O (100 ml) and EtOAc (50 ml) was added and shaken. The aqueous phase was extracted with EtOAc (50 ml) and the combined organic extracts were washed with satd. NaCl solution (50 ml) and then dried with Na$_2$SO$_4$ and evaporated to afford (RS)-6-hydroxy-chroman-2-carboxylic acid as white crystals (0.94 g, 4.84 mmol, 90%) Mp. 175–177° C., MS m/e=194.1 (M$^+$).

Example 77

(RS)-6-Methoxy-chroman-2-carboxylic Acid

A vigorously stirred mixture of 6-methoxychromenone-2-carboxylic acid (2.20 g, 10 mmol) and Pd/C (10%), (300 mg) in acetic acid (200 ml) was heated at 60° C. for 5 hr under an atmosphere of hydrogen. The catalyst was removed and the solution evaporated to afford (RS)-6-methoxy-chroman-2-carboxylic acid (2.04 g, 9.8 mmol, 98%) as yellowish crystals Mp. 131–135° C., MS m/e=208.1 (M$^+$). Lit: N. Cohen et. al. *J. Med Chem.*, 1989, 32, 1842–1860.; and D. T. Witaik et. al, *J. Med. Chem.*, 1971, 14, 758–766.

Example 78

(1RS,2RS)-1-(6-Benzyloxy-1-hydroxy-1,2,3,4-tetrahydro-naphthalen-2-ylmethyl)-4-(4-methyl-benzyl)-piperidin-4-ol (RS)-6-Benzyloxy-2-[4-hydroxy-4-(4-methyl-benzyl)-piperidin-1-ylmethyl]-3,4-dihydro-2H-naphthalen-1-one (1.30 g, 2.77 mmol) in THF (15 ml) was added dropwise to a suspension of LiAlH$_4$ (0.6 g, 15.5 mmol) in THF (20 ml) over 15 min (5–10° C.) and then stirred at RT for 2.5 hr. Distilled H$_2$O (1 ml) and 4N NaOH (2 ml) followed by further H$_2$O (2 ml), was added to quench the reaction and stirred vigorously 15 min., the mixture was then dried with Na$_2$SO$_4$, filtered and evaporated. The resulting crude liquid was chromatographed over SiO$_2$ (Merck 230–400 mesh) eluting with CH$_2$Cl$_2$—MeOH—NH$_4$OH (100:5:0.25) to afford the title compound as a white foam (0.75 g, 1.6 mmol, 57%), MS m/e=472.4 (M+H$^+$).
Following the General Method of Example 78. Example 79 was Prepared

Example 79

(1RS,2RS)-1-(6-Benzyloxy-1-hydroxy-1,2,3,4-tetrahydro-naphthalen-2-ylmethyl)-4-benzyl-piperidin-4-ol The title compound was obtained as a colourless oil MS: m/e=458.6 (M+H$^+$), prepared from (RS)-2-(4-benzyl-4-hydroxy-piperidin-1-ylmethyl)-6-benzyloxy-3,4-dihydro-2H-naphthal-en-1-one.

Example 80

(RS)-6-Benzyloxy-2-[4-hydroxy-4-(4-methyl-benzyl)-piperidin-1-ylmethyl]-3,4-dihydro-2H-naphthalen-1-one 6-Benzyloxy-1-tetralone (1.26 g, 5 mmol), 4-(4-methyl-benzyl)-piperidin-4-ol hydrochloride (1.20 g, 5 mmol) and paraformaldehyde (150 mg, 5 mmol) in DMF (10 ml) were heated at 70° C. for 17 hr. The crude mixture was partitioned between distilled H$_2$O (150 ml), 25% NH$_4$OH (2 ml) and EtOAc (100 ml). The aqueous phase was further extracted with EtOAc (100 ml) and the combined organic extracts washed twice with satd NaCl solution (100 ml), dried Na$_2$SO$_4$ filtered and evaporated to afford an orange oil. Chromatography over SiO$_2$ (Merck 230–400 mesh) eluting with EtOAc-Et$_3$N (19:1) afforded (RS)-6-benzyloxy-2-[4-hydroxy-4-(4-methyl-benzyl)-piperidin-1-ylmethyl]-3,4-dihydro-2H-naphthalen-1-one as an amber oil (1.34 g, 2.85 ml, 57%), MS m/e=470.3 (M+H$^+$).
Following the General Method of Example 80. Example 81 was Prepared

Example 81

(RS)-2-(4-Benzyl-4-hydroxy-piperidin-1-ylmethyl)-6-benzyloxy-3,4-dihydro-2H-naphtalen-1-one The title compound was obtained as a yellow oil MS: m/e=456.6 (M+H$^+$), prepared from 6-benzyloxy-1-tetralone, 4-benzyl-4-hydroxy-piperidine hydrochloride and paraformaldehyde.

Example 82

6-Benzyloxy-1-tetralone

6-Hydroxy-1-tetralone (10 g, 61.65 mmol), benzyl bromide (8.1 ml, 67.82 mmol) and K$_2$CO$_3$ (21.3 g, 154 mmol) in acetone (40 ml) were heated under reflux 2.5 hr. Following filtration and evaporation of the solvent the crude material was acidified to pH1 with 1N HCl and partioned between H$_2$O (150 ml) and EtOAc (150 ml). The aqueous phase was further extracted with EtOAc (100 ml) and the extracts dried (Na$_2$SO$_4$) filtered and evaporated to afford 6-benzyloxy-1-tetralone as an orange solid (12.37 g, 49.3 mmol, 80%) Mp. 97–100° C., MS m/e=252.1 (M$^+$).

Example 83

6-Hydroxy-1-tetralone

6-Methoxy-1-tetralone (80 g, 453 mmol) was taken up in 48% HBr (270 ml) at 4° C., then stirred at ambient temperature for 4 hr. Distilled H$_2$O (1 l) was added with cooling to 4° C. and the precipitated solid was filtered, washed with H$_2$O and recrystallised twice from EtOH-H$_2$O (4:1) to afford 6-hydroxy-1-tetralone as a beige solid (59.7g, 368 mmol, 81%), Mp. 153–155° C., MS m/e=162.1 (M$^+$).

Example 84

(RS)-1-(6-Methoxy-1,2,3,4-tetrahydro-naphthalen-2-ylmethyl)-4-(4-methyl-benzyl)-piperidin-4-ol (RS)-Toluene-4-sulfonic acid 6-methoxy-1,2,3,4-tetrahydro-naphthalen-2-ylmethyl ester (1.32 g, 3.81 mmol) and 4-(methyl-benzyl)-piperidin-4-ol (3.13 g, 15.24 mmol) in mesitylene (100 ml) was heated at 140° C. for 20 hr. Following evaporation of the solvent the crude material was partioned between CH$_2$Cl$_2$ (50 ml) and 5% NaHCO$_3$ (30 ml), the aqueous phase was extracted with CH$_2$Cl$_2$ (2×100 ml) washed with satd. NaCl solution (50 ml), dried (Na$_2$SO$_4$), filtered and evaporated. The crude product was chomatographed over SiO$_2$ (Merck 230–400 mesh) eluting with EtOAc-n-Hexane (1:3) then (1:1), to afford (RS)-1-(6-methoxy-1,2,3,4-tetrahydro-naphthalen-2-ylmethyl)-4-(4-methyl-benzyl)-piperidin-4-ol as a white solid (972 mg, 2.56 mmol, 67.3%), Mp. 91–94° C., MS m/e=380.3 (M+H$^+$).

Example 85

(RS)-Toluene-4-sulfonic Acid 6-methoxy-1,2,3.4-tetrahydro-naphthalen-2-ylmethyl Ester (RS)-(6-methoxy-1,2,3,4-tetrahydro-naphthalen-2-yl)-methanol (939 mg, 4.88 mmol), p-toluenesulfonyl chloride (934 mg, 4.9 mmol), triethylamine (1.12 ml, 7.88 mmol) and N,N-dimethyl aminopyridine (10 mg) in CH$_2$Cl$_2$ (10 ml) was stirred together at ambient temperature for 24 hr. Acidification with 1N HCl (pH 1–2), extraction of the aqueous phase with CH$_2$Cl$_2$ (2×20 ml), drying (Na$_2$SO$_4$) filtration and evaporation afforded the crude product which wag chomatographed over SiO$_2$ (Merck 230–400 mesh) eluting with EtOAc-n-Hexane (1:3) to afford the title compound as a colourless oil (1.37 g, 3.95 mmol, 81%), MS m/e=346.1 (M$^+$).

Example 86

(RS)-(6-Methoxy-1,2,3,4-tetrahydro-naphthalen-2-yl)-methanol (RS)-6-methoxy-1,2,3,4-tetrahydro-naphthalene-2-carboxylic acid ethyl ester (1.39 g, 5.93 mmol) in THF (20 ml) was added dropwise to a suspension of LiAlH$_4$ (473 mg, 12.46 mmol) at 0–10° C. over 15 min. The reaction was stirred for 1 hr at RT, then quenched by the addition of 4N NaOH (15 ml) and water (20 ml). After stirring vigorously for 15 min the mixture was extracted with EtOAc (25 ml), the aqueous phase was further extracted with EtOAc (2×25 ml), the combined organic extracts were washed with satd. NaCl solution (30 ml), dried (Na$_2$SO$_4$) filtered and evaporated to give the crude product as a clear oil. Chromatographic purification over SiO$_2$ (Merck 230–400 mesh) eluting with EtOAc-nHexane (1:3) produced (RS)-(6-methoxy-1,2,3,4-tetrahydro-naphthalen-2-yl)-methanol as a colourless oil (989 mg, 5.14 mmol, 86%), MS m/e=192.1 (M$_-$$^+$).

Example 87

(RS)-6-Methoxyl-1,2,3,4-tetrahydro-naphthalene-2-carboxylic Acid Ethyl Ester (RS)-6-methoxy-1-oxo-1,2,3,4-tetrahydro-naphthalene-2-carboxylic acid ethyl ester (2.0 g, 8.05 mmol) in MeOH (20 ml) and Pd/C (10%), (200 mg) was stirred vigorously under a hydrogen atmosphere for 3 hr at ambient temperature. The catalyst was removed and solvent evaporated to afford an oil, which was purified by chromatography over SiO$_2$ (Merck 230–400 mesh) eluting with EtOAc-nHexane (1:9) to afford (RS)-6-methoxy-1,2,3,4-tetrahydro-naphthalene-2-carboxylic acid ethyl ester as a colourless oil (1.88 g, 6.14 mmol, 76%), MS ml/e=234.1 (M$^+$).

Example 88

(RS)-6-Methoxy-1-oxo-12,3 4-tetrahydro-naphthalene-2-carboxylic Acid Ethyl Ester 6-Methoxy-tetralone (10 g, 56.75 mmol), diethylcarbonate (20.6 ml, 170.2 mmol) and sodium hydride (5.06 g, 210.8 mmol) were heated together at 65° C. in THF (400 ml) for 18 hr. After cooling glacial acetic acid (15 ml, 250 mmol) was added cautiously followed by toluene (2×200 ml) then co-evaporated to remove excess acetic acid. The residue was taken up in EtOAc (400 ml), H$_2$O (400 ml) and shaken, the aqueous phase was extracted with EtOAc (2×100 ml) and the combined organic extracts washed with satd. NaCl solution (100 ml), dried (Na$_2$SO$_4$), filtered and washed. The crude product was crystallised from EtOAc-nHexane to afford the title compound as a yellow solid (8.3 g, 33.4 mmol, 58%), MS m/e=248.1 (M$^+$).

What is claimed is:

1. A compound of the formula

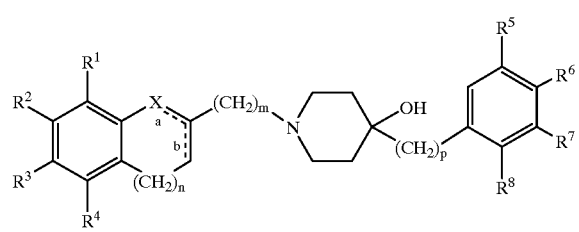

I wherein

X denotes —NH—;

R$^1$–R$^4$ are, independently from each other hydrogen, hydroxy, lower-allyl-sulfonylamino, 1- or 2-imidazolyl or acetamido;

R$^5$–R$^8$ are, independently from each other hydrogen, hydroxy, lower-alkyl, halogen, lower-alkoxy, trifluoromethyl or trifluoromethyloxy;

a and b are, independently from each other, double bonds or not, wit the proviso that when "a" is a double bond, "b" cannot be a double bond;

n is 1 or 2;

m is 1–3;

p is 0 or 1 and pharmaceutically acceptable addition salts thereof.

2. A compound according to claim 1, wherein the compound is:

(RS)-2-[4-hydroxy-4-(4-methyl-benzyl)-piperidine-1-ylmethyl]-2,3-dihydro-1H-indol-5-ol.

* * * * *